(12) United States Patent
Owen

(10) Patent No.: US 6,485,450 B1
(45) Date of Patent: Nov. 26, 2002

(54) BRAIN RESUSCITATION APPARATUS AND METHOD

(75) Inventor: Donald R. Owen, New Orleans, LA (US)

(73) Assignee: Life Science Holdings, Inc., Chicago, IL (US)

( * ) Notice: Subject to any disclaimer, the term of this patent is extended or adjusted under 35 U.S.C. 154(b) by 0 days.

(21) Appl. No.: 09/039,557

(22) Filed: Mar. 16, 1998

(51) Int. Cl.[7] .............................................. A61M 37/00
(52) U.S. Cl. ......................... 604/24; 604/28; 604/507; 128/898
(58) Field of Search .......................... 128/898; 604/152, 604/24, 507, 28, 4

(56) References Cited

U.S. PATENT DOCUMENTS

| | | |
|---|---|---|
| 1,682,344 A | 8/1928 | Lesieur |
| 1,916,658 A | 7/1933 | Davidson |
| 3,406,531 A | 10/1968 | Swenson et al. |

(List continued on next page.)

FOREIGN PATENT DOCUMENTS

| | | |
|---|---|---|
| DE | 221 361 A1 | 4/1985 |
| DE | A1-221361 | 4/1985 |
| EP | A1-0265082 | 4/1988 |
| EP | A2-0297723 | 1/1989 |
| JP | A-1-213276 | 8/1989 |
| SU | 760972 | 9/1980 |
| SU | 852335 | 8/1981 |
| SU | A1-1632428 | 3/1991 |
| WO | WO 92/06681 | 4/1992 |
| WO | WO 96/13288 | 5/1996 |
| WO | WO 96/32074 | 10/1996 |
| WO | WO 96/32157 | 10/1996 |

OTHER PUBLICATIONS

"Cerebral Blood Flow, Vasoreactivity, and Oxygen Consumption During Barbiturate Therapy in Severe Traumatic Brain Lesions", by Carl–Henrik Nordström, MD et al., *J. Neurosurg*, vol. 68, Mar. 1988, pp. 424–431.

"At Surgery's Frontier: Suspended Animation", by Elisabeth Rosenthal, *The New York Times*, Nov. 13, 1990, pp. C1, C12.

"Randomized Clinical Study of Thiopental Loading in Comatose Survivors of Cardiac Arrest", *The New England Journal of Medicine*, vol. 314, No. 7, Feb. 13, 1986, pp. 397–403.

"Current Concepts in Brain Resuscitation", By Mark C. Rogers, MD, *Journal of the American Medical Association*, vol. 261, No. 21, Jun. 2, 1989, pp. 3143–3147.

(List continued on next page.)

*Primary Examiner*—V. Millin
*Assistant Examiner*—Kelly O'Hara
(74) *Attorney, Agent, or Firm*—Oliff & Berridge PLC

(57) ABSTRACT

A resuscitation apparatus includes a fluid pathway in fluid communication with a source of medical fluid, an interface unit for attaching the fluid pathway to the cardiovascular system of a mammal suffering from impaired blood flow in order to establish an artificial circulation in the mammal utilizing the medical fluid, and heat exchange apparatus that provides intense cooling to quickly chill the medical fluid a sufficient amount to slow a metabolic rate of an organ of a mammal into which the medical fluid is introduced. A method of treating anoxic and/or ischemic brain injury in a mammal suffering from impaired blood flow includes utilizing heat exchange apparatus that provides intense cooling to quickly chill a medical fluid a sufficient amount to slow a metabolic rate of a brain of a mammal into which the medical fluid is introduced, and introducing the chilled medical fluid into the cardiovascular system of a mammal suffering from impaired blood flow in order to establish an artificial circulation in the mammal, whereby the mammal remains substantially neurologically intact.

37 Claims, 12 Drawing Sheets

U.S. PATENT DOCUMENTS

| | | | |
|---|---|---|---|
| 3,632,473 | A | 1/1972 | Belzer et al. |
| 3,881,483 | A | 5/1975 | Sausse |
| 3,962,439 | A | 6/1976 | Yokoyama et al. |
| 4,314,143 | A | 2/1982 | Bilstad et al. |
| 4,378,797 | A | 4/1983 | Osterholm |
| 4,393,863 | A | 7/1983 | Osterholm |
| 4,445,500 | A | 5/1984 | Osterholm |
| 4,451,251 | A | 5/1984 | Osterholm |
| 4,582,598 | A | 4/1986 | Bilstad et al. |
| 5,013,303 | A | 5/1991 | Tamari et al. |
| 5,028,588 | A | 7/1991 | Hoffman et al. |
| 5,036,097 | A | 7/1991 | Floyd et al. |
| 5,047,395 | A | 9/1991 | Wu |
| 5,130,230 | A | 7/1992 | Segall et al. |
| 5,145,771 | A | 9/1992 | Lemasters et al. |
| 5,149,321 | A | 9/1992 | Klatz et al. |
| 5,200,176 | A | 4/1993 | Wong et al. |
| 5,216,032 | A | 6/1993 | Manning |
| 5,217,860 | A | 6/1993 | Fahy et al. |
| 5,234,405 | A | 8/1993 | Klatz et al. |
| 5,338,662 | A | 8/1994 | Sadri |
| 5,383,854 | A | 1/1995 | Safar et al. |
| 5,395,314 | A | 3/1995 | Klatz et al. |
| 5,437,633 | A | 8/1995 | Manning |
| 5,494,822 | A | 2/1996 | Sadri |
| 5,584,804 | A | 12/1996 | Klatz et al. |
| 5,879,329 | A | 3/1999 | Ginsburg |

OTHER PUBLICATIONS

"Cerebrovascular Hypoxic and Autoregulatory Responses During Reduced Brain Metabolism," by Judith H. Donegan et al., *The American Physiological Society*, (1985), vol. 249, pp. H421–H429.

"Regional Cerebral Blood Flow in Normal Blood Circulated and Perfluorocarbon Transfused Rats", *Advances in Experimental Medicine and Biology*, (1986), vol. 200, pp. 59–65.

"Protection from Cerebral Air Emboli with Perflurorocarbons in Rabbits", Bruce D. Spiess, MD, et al., *Stroke*, vol. 17, No. 6, Nov.–Dec. 1986, pp. 1146–1449.

"Free Radicals and Myocardial Ischemia and Reperfusion Injury", by Paul J. Simpson, *J. Lab. Clin, Med.*, Jul. 1987, pp. 13–30.

"Increases in Brain Tumor and Cerebral Blood Flow by Blood–Perfluorochemical Emulsion (Flousol–DA) Exchange", by Shoju Hiraga et al., *Cancer Research*, vol. 47, No. 12, Jun. 15, 1987, pp. 3296–3302.

"Polarographic Cerebral Oxygen Availability, Flourocarbon Blood Levels and Efficacy of Oxygen Transport by. Emulsions", by Leland C. Clark, Jr. et al., *Biomaterials*, 16(1–3), (1988), pp. 375–393.

"The Nature of Flourocarbon Enhanced Cerebralk Oxygen Transport", by Leland C. Clark, Jr. et al., *Advances in Experimental Medicine and Biology*, vol. 248, pp. 341–355.

"Easier Breathing in RDS", *Medical Tribune*, Jan. 11, 1990, p. 2.

"Cerebral Ischemic Injury", by Blaine C. White, *Resuscitative Problems and Techniques*, (1978), pp. 9–10.

"90s Could See Brain Injury Reversal", American Medical News, Nov. 17, 1989, p. 66.

"Cooling Brain May Limit Stroke Damage", *American Medical News*, Nov. 17, 1989, p. 66.

"Drug May Preserve Heart Tissue After Attack", *New York Times*, Sep. 5, 1989, p. 3.

"Radical Therapy", by Karen Wrig, *Scientific American*, Sep. 1987.

"Diseases of the Central Nervous System", *Asbury, McKhann, McDonald*, (1986), pp. 1072 and 1083.

"Resuscitation of the Rabbit Brain After Acute Complete Ischemia Lasting Up to One Hour: Pathophysiological and Pathomorphological Observations", by Ryszard Pluta, *Resuscitation* 15, (1987), pp. 267–287.

"The Use of Blood Substitutes for Whole body Perfusion in Ultra–Profound Hypothermic Cardiac Arrest", Amr M. Elrifai et al., vol. 20, No. 4, Jul.–Aug. 1990, p. 292.

"Nutritional Aspects of Ambulatory Care", *American Family Physicians*, vol., 42, No. 3, Sep. 1990, pp. 557–558.

"In Situ Cadaver Kidney Perfusion", by Robert T. Schweizer et al., *Transplantation, Official Journal of the Transplantation Society*, vol. 32, No. 6, Dec. 1981, pp. 482–484.

"In situ kidney preservation for transplantation with use of profound hypothermia (5 to 20°C.) with an intact circulation", by A.R. Moossa et al., *Surgery*, vol. 79, No.1, Jan. 1976, pp. 60–64.

"Extracorporeal perfusion for obtaining postmortem homografts", by T.L. Marchioro, M.D. et al., *Surgery*, vol. 54, No. 6, Jul.–Dec. 1963, pp. 900–911.

"Use of Extracoporeal Cadaver Perfusion for Preparation of Organ Homografts", by T. L. Marchioro, M.D., *Surgical Forum*, vol. XIV, Oct. 1963, pp. 174–176.

Robert J. White, Preservation of Cerebral Function During Circulatory Arrest and Resuscitation: Hypothermic Protective Considerations, Resuscitation, I, pp. 107–115, 1972.

"Arrest of cerebral blood flow and reperfusion of the brain in the rhesus monkey", by L.R. Wolin et al., *Resuscitation*, (1972) vol. I., pp. 39–44.

"Long–Life Dream—A Window to Survival", Longevity, Dec. '89/Jan. '90 (1–page).

"The Art of Staying Alive", by Vic Sussman, U.S. News & World Report, Oct. 18, 1993, pp. 70–71.

"New Device May Save Brains Being Lost in Cardiac Arrest", Dr. Ronald Klatz et al., Nov. 4 and 11, 1989.

"Donor Core–Cooling Provides Improved Static Preservation for Heart–Lung Transplantation", by Charles D. Fraser, Jr., M.D. et al., *The Annals of Thoracic Surgery*, vol. 45, No. 3, Mar. 1988, pp. 253–257.

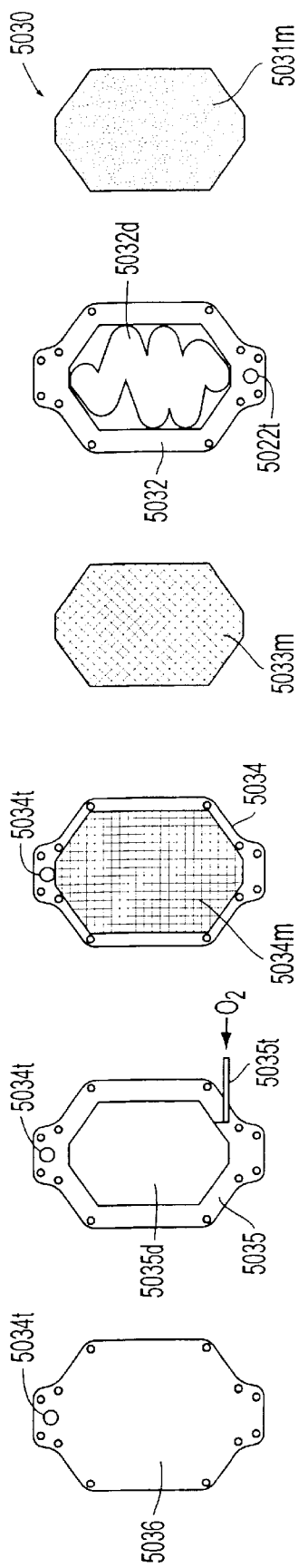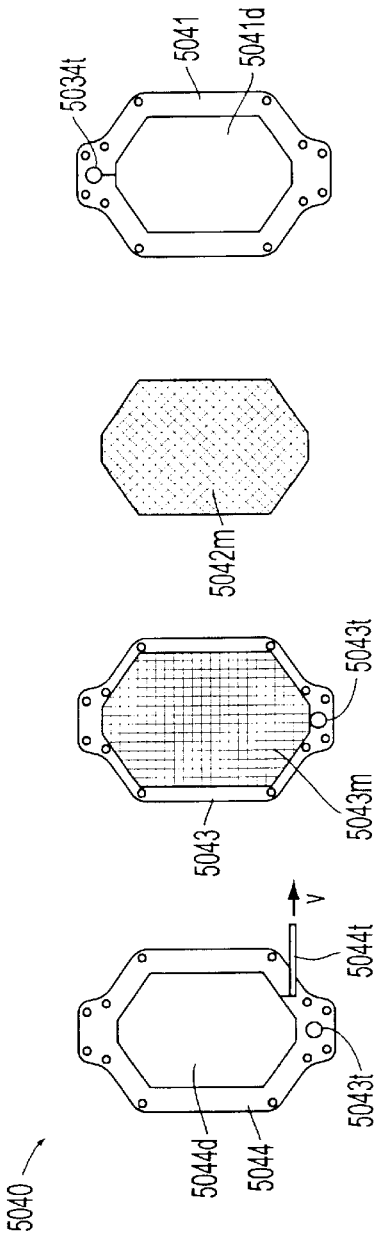
FIG. 11
FIG. 12

BRAIN RESUSCITATION APPARATUS AND METHOD

BACKGROUND OF THE INVENTION

1. Field of Invention

The invention relates to a resuscitation apparatus and method for directing a chilled medical fluid to the brain at a sufficient rate to allow a rapid drop in overall brain temperature. The apparatus and method extend the period of time in which life resuscitation methodologies may be performed on a patient suffering from trauma or decreased blood flow to the brain, without permanent brain damage resulting if recovery is achieved.

2. Description of Related Art

When trauma or decreased blood flow to the brain occurs, the brain is deprived of freshly oxygenated blood. For example, this situation typically occurs during cardiac arrest, respiratory arrest, stroke and other cerebrovascular trauma, suffocation, drowning, strangulation, electrocution, toxic poisoning (carbon monoxide, cyanide, etc.), metabolic insults or other similar trauma. Without a steady supply of freshly oxygenated blood, the brain ceases to function. After resuscitation, most patients will suffer some damage to the brain and associated neurologic tissues.

For example, among cardiac arrest victims overall less than 10% survive neurologically intact and without significant brain damage. The other approximately 90% either die or sustain some neurologic injury from ischemia (i.e., lack of blood flow to the brain) or anoxia (i.e., lack of oxygen to the brain). Such frequency of neurologic injury occurs because after a cardiac arrest, basic cardiopulmonary resuscitation and advanced life support techniques, such as CPR, closed heart cardiac chest massage, and electroshock treatments, typically require fifteen to twenty minutes to regain circulation from a failed heart. Reversible neurologic damage begins as early as four minutes and irreversible neurologic damage begins as early as six minutes after circulation stops. To combat this potential neurologic injury, initial resuscitation efforts need to be directed toward reviving and/or preserving the viability of the brain in addition to resuscitating the heart.

Anoxic and ischemic brain injuries from cardiac arrest result in damage to the brain and associated neurologic tissues after about four minutes. In contrast, the heart can survive intact up to four hours after cardiac arrest. The short viability of brain tissue upon deprivation of oxygenated blood is a result of the requirement of high amounts of nutrients for tissue maintenance. Brain tissue uses for maintenance almost all of the nutrients supplied to it by the circulating blood, and stores only a very small amount of nutrients. Absent blood flow to the brain, the small amount of stored nutrients is rapidly exhausted. Once the stored nutrients are exhausted, brain oxygen content rapidly depletes. This oxygen depletion is traumatic and causes a series of reactions in the oxygen starved brain tissue cells. These reactions are believed to produce free radical ions, primarily consisting of the superoxide radical $O_2^-$. These free radicals complex with proteins in the brain and associated neurologic tissues, altering respiration, energy transfer and other vital cellular functions, and irreversibly damaging these tissues.

Efforts should be directed toward extending the period of time the brain can function without oxygen while the patient remains neurologically intact.

The medical literature is replete with examples of humans surviving extended periods of time (greater than 5 minutes) without oxygen being delivered to the brain. For example, children revived after hours of submersion in very cold water have fully recovered with little if any neurologic damage.

Hypothermic therapy is one method of keeping the brain alive absent oxygen. It involves cooling the brain to a temperature where its metabolic activity is decreased. When the brain's metabolic activity is decreased, it uses much less oxygen and more slowly exhausts stored nutrients, while production of irreversibly damaging $O_2^-$ free radicals is slowed and almost completely ceased. Thus, upon resuscitating the body from trauma, the patient emerges neurologically intact. The literature has demonstrated that a drop of 3–4 degrees Celsius can be sufficient to protect the brain from irreversible damage in a hypoxic state for at least 10–20 minutes.

Various apparatus and/or methods have previously been disclosed for directing a chilled medical fluid to the brain to prevent anoxic and/or ischemic injury during trauma.

In the article, "Preservation of Cerebral Function During Circulatory Arrest and Resuscitation: Hypothermic Protective Considerations", Robert M. White teaches delivering chilled fluids to the brain via the carotid arteries. According to the White method, the carotid arteries are punctured with Rochester no. 15 needles connected via plastic tubing to intravenous bottles containing cooled perfusate. The fluids are delivered at an average pressure of 75 mm mercury by an attached standard sphygmomanometer bulb. The fluids taught include saline, dextran and oxygenated blood.

Russian Patent No. 760,972 to Raduschkevi et al. discloses apparatus for cooling the brain during a sudden stoppage of the heart or an ineffective functioning of the heart. The apparatus includes a refrigeration unit that includes a heat-insulated chamber for cooling a blood-mixed fluid; a heat exchanger; a filter/trap; a perfusion pump; cannulae for connecting to blood vessels; and means for control and regulation of temperature and fluid transport. Blood from an artery can also be withdrawn through a tube, circulated through the apparatus, passing through the perfusion pump, the heat exchanger and the filter trap, and returned to the artery via a tube.

In U.S. Pat. No. 4,451,251, Osterholm discloses an apparatus and method for circulating a nutrient emulsion through the cerebrospinal fluid pathway system to satisfy cerebral metabolic needs where the vascular system has been obstructed. Osterholm teaches injecting the nutrient emulsion via cerebral catheter means directly into a cerebral ventricle. Osterholm further teaches that hypothermic temperatures may be selected for the nutrient emulsion in order to establish certain treatment conditions if so desired. The apparatus includes a nutrient emulsion reservoir, a heat exchanger, an oxygenator, a filtration device and the cerebral catheter means.

In U.S. Pat. Nos. 5,149,321, 5,234,405 and 5,395,314 and co-pending U.S. patent application Ser. No. 08/484,601 now U.S. Pat. No. 5,827,222, Ronald M. Klatz and Robert M. Goldman disclose a brain resuscitation device and corresponding method. The device includes a solution reservoir, an oxygenator, a heat exchanger, a fluid pathway and a catheter. The catheter may be a balloon catheter. The solution may include barbiturates, free radical scavengers and/or oxygen carrying agents. Further, the device may be portable.

However, none of these references provide heat exchange apparatus that provides intense cooling to quickly chill a medical fluid a sufficient amount to slow a metabolic rate of a brain of a mammal into which the medical fluid is introduced. Further, none of them provides a convenient portable apparatus. Furthermore, none discloses docking apparatus that allows the portable apparatus to be removably attached to a heat exchange apparatus in order to maintain a medical fluid chilled an amount sufficient to slow a metabolic rate of a brain of a mammal into which the medical fluid is introduced until the portable apparatus is needed. Additionally, none discloses a control unit that controls the introduction of medical fluid into the system to prime the system prior to introducing the medical fluid into a mammal.

SUMMARY OF THE INVENTION

The apparatus and method according to the invention extend the period of time in which life resuscitation methodologies may be performed on a patient suffering from trauma or decreased blood flow to the brain, without permanent brain damage resulting if recovery is achieved. Because emergency personnel often must treat patients suffering from trauma or decreased blood flow to the brain without the conveniences of a hospital, sometimes an apparatus is needed that can be carried with emergency personnel to the patient and be ready upon demand.

The apparatus and method according to the invention can utilize heat exchange apparatus that provide intense cooling to quickly chill a medical fluid a sufficient amount to slow a metabolic rate of a brain or other organ of a mammal into which the medical fluid is introduced, or alternatively, the resuscitation apparatus can be provided with docking apparatus that allows the portable apparatus to be removably attached to a heat exchange apparatus in order to maintain the medical fluid chilled an amount sufficient to slow a metabolic rate of an organ of a mammal into which the medical fluid is introduced until the portable apparatus is needed. Accordingly, the apparatus can provide the necessary cooling on demand, and, if optionally configured to be portable, can be carried to the patient. The apparatus is particularly applied to slow the metabolic rate of the brain but can be used to slow the metabolic rate of other organs depending on the location of entry in the cardiovascular system.

Further, medical fluids are expensive, and, away from the conveniences of a hospital, may be in short supply. The apparatus and method according to the invention can withdraw medical fluid from a mammal, degas, oxygenate and/or chill the medical fluid before reintroducing the medical fluid into the mammal. Accordingly, less medical fluid is needed.

Additionally, the apparatus and method can utilize a control unit to prime the system prior to introducing medical fluid into a patient. This allows medical personnel to focus more of their attention on life resuscitation methodologies which they are performing to revive the patient.

BRIEF DESCRIPTION OF THE DRAWINGS

These and other aspects and advantages of the invention will become apparent from the following detailed description of embodiments when taken in conjunction with the accompanying drawings, in which:

FIG. 11 is an exploded view of an oxygenation module of a combined pump, filtration, oxygenation and/or debubbler apparatus according to the invention;

FIG. 12 is an exploded view of a debubbler module of a combined pump, filtration, oxygenation and/or debubbler apparatus according to the invention;

DETAILED DESCRIPTION OF PREFERRED EMBODIMENTS

Figure 1:
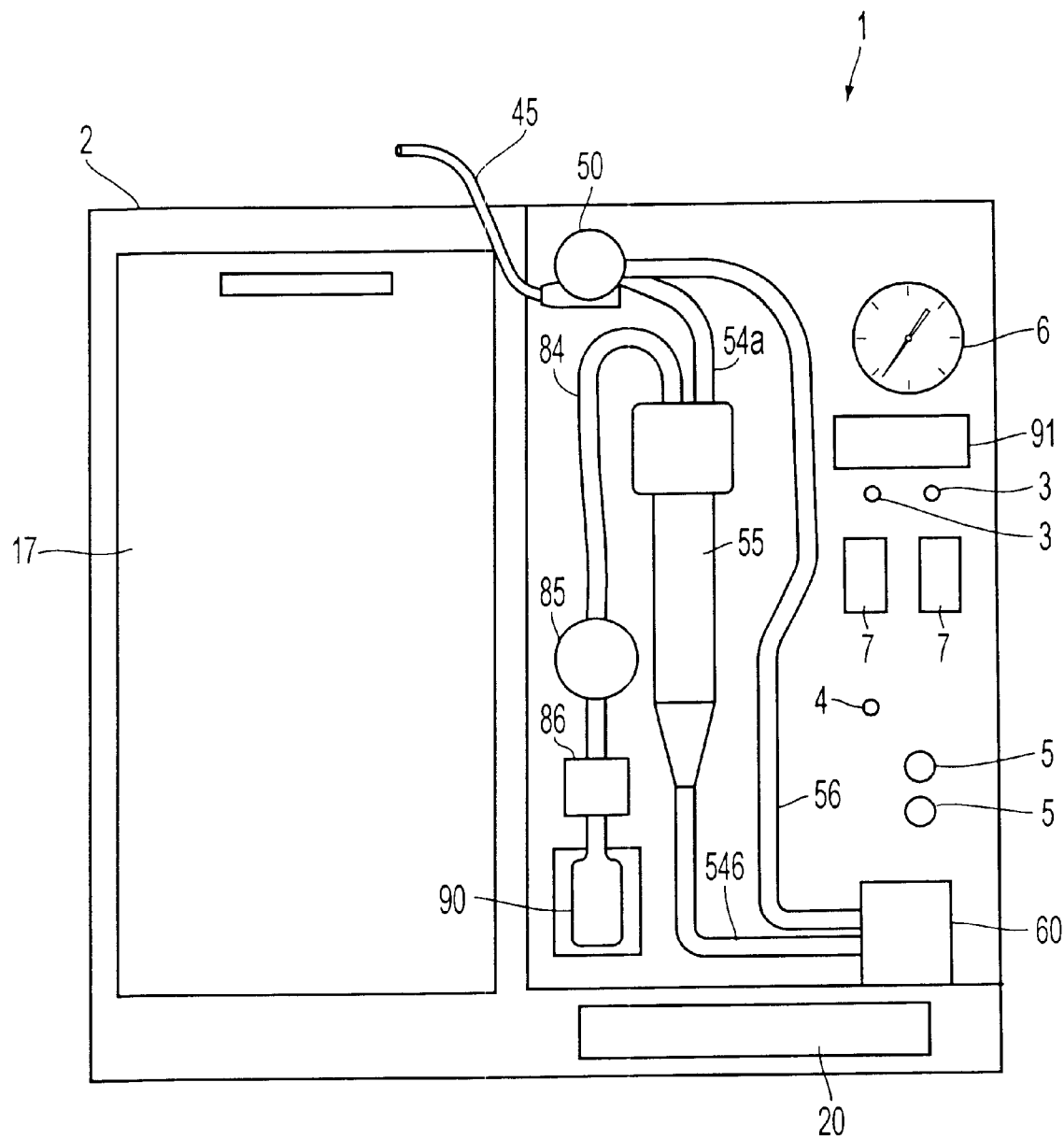
FIG. 1 is a front view of a resuscitation apparatus according to the invention.

The invention provides a resuscitation apparatus that can quickly chill a medical fluid a sufficient amount to slow a metabolic rate of a brain and other organs of a mammal into which the medial fluid is introduced.

The invention further provides a portable resuscitation apparatus which includes docking apparatus that allows the portable apparatus to be removably attached to a heat exchange apparatus in order to maintain the medical fluid chilled an amount sufficient to slow a metabolic rate of an organ of a mammal into which the medical fluid is introduced until the portable apparatus is needed.

The invention also provides a portable resuscitation apparatus that includes a control unit that controls the introduction of medical fluid into the system to prime the system prior to introducing the medical fluid into a mammal.

The invention additionally provides a resuscitation apparatus that can recirculate a medical fluid withdrawn from a mammal and reintroduce the medical fluid into the mammal.

The invention includes a method of reducing anoxic and/or ischemic brain injury in a mammal suffering from impaired blood flow. The method comprises utilizing heat exchange apparatus that provides intense cooling to quickly chill a medical fluid a sufficient amount to slow a metabolic rate of a brain of a mammal into which the medical fluid is introduced, and introducing the chilled medical fluid into the cardiovascular system of a mammal suffering from impaired blood flow in order to establish an artificial circulation in said mammal, whereby the mammal remains substantially neurologically intact. All blood contact surfaces are preferably formed of or coated with non-thrombogenic materials. The medical fluid may be introduced into the cardiovascular system from a pressurized reservoir. Depending on the point of introduction into the cardiovascular system, the metabolic rate of other organs can be slowed as well. The reservoir may be pressurized by activating a pressure cuff surrounding the reservoir; however, other ways of pressurizing the reservoir may also be acceptable.

The medical fluid may be passed through the heat exchange apparatus as the medical fluid is passed back and forth between at least two containers of reservoir to chill the medical fluid a sufficient amount to slow a metabolic rate of the organ of a mammal prior to introducing the chilled medical fluid into the cardiovascular system. The heat exchange apparatus may for example utilize expansion of a cryogenic fluid in a non-recirculating expansion chamber to chill the medical fluid.

The method may further include withdrawing medical fluid from the mammal, circulating the withdrawn medical fluid through the heat exchange apparatus; and reintroducing the medical fluid into the mammal. A recirculation pump and a recirculation heat exchange apparatus may be provided in fluid communication with the recirculation fluid pathway, and the medical fluid withdrawn from the mammal may be passed through the recirculation heat exchange apparatus in order to chill the medical fluid a sufficient amount to slow a metabolic rate of an organ of a mammal. Further, the method may include oxygenating and degassing the medical fluid withdrawn from the mammal prior to reintroducing the medical fluid into the mammal.

According to another embodiment of the invention, the method of reducing anoxic and/or ischemic brain injury in a mammal suffering from impaired blood flow may include removably attaching a portable resuscitation apparatus to a heat exchange apparatus in order to maintain medical fluid within the apparatus chilled a sufficient amount to slow a metabolic rate of a brain of a mammal into which the medical fluid is introduced, detaching the portable resuscitation apparatus from the heat exchange apparatus, and introducing chilled medical fluid from the detached portable resuscitation apparatus into the cardiovascular system of a mammal suffering from impaired blood flow in order to establish an artificial circulation in the mammal utilizing the medical fluid.

According to yet another embodiment of the invention, the method of reducing anoxic and/or ischemic brain injury in a mammal suffering from impaired blood flow may include removably attaching a portable resuscitation apparatus having a medical fluid reservoir, a fluid pathway in fluid communication with the reservoir and an interface unit for attaching the fluid pathway to the cardiovascular system of a mammal to a heat exchange apparatus in order to maintain medical fluid within the apparatus chilled a sufficient amount to slow a metabolic rate of an organ of a mammal into which the medical fluid is introduced, detaching the portable resuscitation apparatus from the heat exchange apparatus, and introducing chilled medical fluid from the reservoir into the fluid pathway to prime the fluid pathway prior to allowing fluid communication between the fluid pathway and the interface unit to introduce chilled medical fluid from the detached portable resuscitation apparatus into the cardiovascular system of a mammal suffering from impaired blood flow in order to establish an artificial circulation in the mammal utilizing the medical fluid.

The resuscitation apparatus according to the invention may include a fluid pathway in fluid communication with a source of medical fluid, an interface unit for attaching the fluid pathway to the cardiovascular system of a mammal suffering from impaired blood flow in order to establish an artificial circulation in the mammal utilizing the medical fluid, and heat exchange apparatus that provides intense cooling to quickly chill the medical fluid a sufficient amount to slow a metabolic rate of an organ of a mammal into which the medical fluid is introduced. The source of medical fluid may be a reservoir in fluid communication with the fluid pathway. The apparatus may further include a pressure source for pressurizing the medical fluid within the reservoir. Preferably the reservoir includes at least one bag of medical fluid and the pressure source includes a compressor or compressed gas tank in fluid communication with a pressure cuff disposed around the bag.

The heat exchange apparatus preferably utilizes expansion of a cryogenic fluid in a non-recirculating expansion chamber to chill the medical fluid. The chamber may include at least one wall formed of a material having high thermal conductivity and high resistivity to low temperature, and the heat exchange apparatus may further include a fluid path assembly adjacent the chamber for circulating therethrough the medical fluid. Further, the apparatus may include at least two containers, the heat exchange apparatus may include a cryogenic fluid heat exchange apparatus between and in fluid communication with both of the containers to permit chilling of the medical fluid through the cryogenic fluid heat exchange apparatus as the medical fluid is passed back and forth between the at least two containers prior to introducing the medical fluid into the fluid pathway.

The apparatus may also include a control valve within the fluid pathway which is shiftable between a position in which medical fluid flows through the fluid pathway to prime the fluid pathway and a position in which the medical fluid is directed through the fluid pathway to the interface unit to be introduced into a mammal.

According to another preferred embodiment of the invention, the apparatus may further include a recirculation fluid pathway in fluid communication with the fluid pathway, and a recirculation interface unit for attaching the recirculation fluid pathway to a blood vessel of the mammal. Also, the apparatus may include a recirculation pump, a recirculation heat exchange apparatus and a combined pump filtration, oxygenation and/or debubbler apparatus in fluid communication with the recirculation fluid pathway. The combined pump filtration, oxygenation and/or debubbler apparatus may be formed of a plurality of stackable support members assembled to form one or more modules, each module capable of one of pumping, filtering, oxygenating and debubbling a fluid. Additionally, the modules may include a filtration module, an oxygenation module, a debubbler module and one or more pump modules. A control valve may also be provided which is shiftable between a position in which medical fluid is diverted from the fluid pathway into the recirculation fluid pathway to prime the recirculation fluid pathway, and a position in which medical fluid is blocked from passing directly from the fluid pathway into the recirculation fluid pathway.

Preferably the recirculation heat exchange apparatus utilizes expansion of a compressed cryogenic fluid in a non-recirculating expansion chamber to chill the medical fluid. The chamber may include at least one wall formed of a material having high thermal conductivity and high resistivity to low temperature, and the recirculation heat exchange apparatus may further include a fluid path assembly adjacent the chamber for circulating therethrough medical fluid.

According to another embodiment of the invention, the resuscitation apparatus may be portable (e.g., sufficiently lightweight to be carried by one person) and include a portable casing, a reservoir disposed within the portable casing for holding therein a medical fluid, a fluid pathway disposed within the portable casing and in fluid communication with the reservoir, an interface unit for attaching the fluid pathway to the cardiovascular system of a mammal suffering from impaired blood flow in order to establish an artificial circulation in the mammal, and docking apparatus that allows the portable resuscitation apparatus to be removably attached to a heat exchange apparatus in order to maintain the medical fluid within the reservoir chilled an amount sufficient to slow a metabolic rate of an organ of a mammal into which the medical fluid is introduced until the portable resuscitation apparatus is needed. The heat exchange apparatus of this embodiment is preferably a thermoelectric device; however, other types of cooling devices may also be appropriate.

According to another embodiment of the invention, the resuscitation apparatus may be portable and include a portable casing, a reservoir disposed within the portable casing for holding therein a medical fluid, a fluid pathway at least partially disposed within the portable casing and in fluid communication with the reservoir, an interface unit for attaching the fluid pathway to the cardiovascular system of a mammal suffering from impaired blood flow in order to establish an artificial circulation in said mammal, heat exchanger apparatus in fluid communication with the reservoir for chilling medical fluid within the reservoir a sufficient amount to slow a metabolic rate of an organ of a mammal into which the medical fluid is introduced, and a control unit that controls the introduction of medical fluid from the reservoir into the fluid pathway to prime the fluid pathway prior to allowing fluid communication between the fluid pathway and the interface unit.

A preferred embodiment of the invention is now discussed in detail with reference to the drawings. In the drawings, like reference numerals have been used throughout to designate like elements.

FIG. 1 is a front view of a resuscitation apparatus 1 according to the invention. The apparatus is preferably at least partially microprocessor controlled, and pneumatically actuated.

The apparatus 1 includes outer casing 2. A drawer 17, which may, for example, be the pull-out or tilt type, is provided to hold a supply of medical fluid, such as the reservoir 10 shown in FIG. 2, and optional modules for cooling the medical fluid, which will be discussed later. A primary infusion tube 45 is provided for connection of the supply of medical fluid to the perfusion pathway formed of tubes 54a, 54b and 56. Infusion of medical fluid into the perfusion pathway is controlled by control valve 50. Tubes 54a, 54b and 56 connect the primary infusion tube 45 and control valve 50 to the catheter interface unit 60. A debubbling/flush chamber 55 is interposed between tubes 54a, 54b. An overflow bag 90, air/fluid sensor 86 and solenoid valve 85 for shifting between prime and flow modes are connected to the debubbling/flush chamber 55 via tube 84.

The apparatus is powered by a power source 91, for example, a 12V battery. The apparatus 1 can also be provided with system pressurize and infuse buttons 7, a system pressure indicator 6, visual signal indicators 3 for indicating system status, a speaker 4 for audible signals and plug-in ports 5 for temperature, flow and pressure sensors.

One embodiment of the resuscitation apparatus 1 according to the invention will now be explained with reference to FIG. 2.

This embodiment, hereinafter the direct infusion option, allows a predetermined amount of medical fluid to be delivered to the brain, at a given flow rate and maximal infusion pressure, via an appropriate blood vessel. The preferred vessels include the jugular vein, carotid artery or femoral artery. However, the invention is not intended to be limited thereto. Specific catheter or catheters 75 are selected based on the entry site. Further, the amount of medical fluid to be delivered is also selected based on the entry site. The catheters are attached to the apparatus via the catheter interface unit 60, which includes a preferably manual valve 62 that provides fluid communication between the catheter 75 and the perfusion pathway when manually activated. The entry site, of course, affects which organs, along with the brain, are cooled. For example, as readily recognized by medical personnel, introduction of the fluid in the femoral artery will slow the metabolic rate of the heart.

As discussed above, the primary infusion tube 45 provides connection of the supply of medical fluid to the perfusion pathway. The reservoir 10 preferably holds 2–3 standard one liter infusion bags 15 with pressure cuffs 16. A pressure source 20 can be provided for pressurizing the medical fluid in the reservoir 10. The pressure source 20 is preferably pneumatic and may be an on board compressor unit 21 supplying at least 10 LPM external cuff activation via gas tube 26, as shown in FIG. 2. Gas valves 22–26 are provided along the gas tube 26 to allow for control of the pressure provided by the onboard compressor 21. An anti-back flow valve 44 is also provided on gas tube 26. The invention, however, is not limited to use of an on board compressor as any adequate pressure source can be employed, for example, a compressed gas (e.g., air, $CO_2$, oxygen, nitrogen, etc.) tank (not shown) preferably with a tank volume of 1.5 liters at 100 psi or greater for internal pressurization. Alternatively, a reservoir tank (not shown) can be used which could be internally pressurized.

A pressure sensor P1 is provided which relays conditions within the compressed gas pathway and a pressure sensor P2 is provided which relays pressure conditions within the perfusion pathway to a microprocessor (not shown) which in turn adjusts the compressor voltage (or the tank valve pressure) and controls gas valves 22–25 in order to maintain a pre-determined flow rate (i.e., pressure to total circuit restrictions). An additional pressure sensor P3 prevents over pressurization within the perfusion pathway, as discussed later. Anti-back flow valves 42, 43 may also be provided on the perfusion pathway.

The medical fluid may, for example, be blood or a simple crystalloid solution, which may be augmented with an appropriate oxygen carrier. The oxygen carrier may, for example, be washed, stabilized red blood cells, cross-linked hemoglobin or fluorocarbon based emulsions. The medical fluid may also contain antioxidants known to reduce peroxidation or free radical damage in the physiological environment and specific agents known to aid in cerebral protection. Thus, cold solutions with oxygen capacities equal to or greater than blood can be rapidly introduced into the cerebral vasculature of a patient in cardiac distress with little or no cardiac output. U.S. Pat. Nos. 5,149,321, 5,234,405 and 5,395,314 and co-pending U.S. patent application Ser. No. 08/484,601, which disclose various combinations of solutions for brain resuscitation apparatus are hereby incorporated by reference.

The medical fluid is cooled to a predetermined temperature (to provide a preferred inflow temperature of ~0.5–20°

C.) by a cryogenic fluid heat exchange apparatus 35, which in module form can be inserted into drawer 17. Cryogenic fluids, such as compressed gaseous or liquid nitrogen or carbon dioxide, are capable of absorbing very large amounts of heat to produce very low temperatures in adjacent materials when they change from one state to another, for example, from a liquid or solid state to a gaseous state. In addition, when a compressed cryogenic fluid is allowed to expand, its temperature decreases and the cryogenic fluid is capable of cooling adjacent materials by absorbing heat from the materials as the compressed fluid expands. The cryogenic fluid heat exchange apparatus of the present application utilizes a compressed cryogenic fluid source to provide a predetermined controlled temperature capable of cooling (e.g., "intense" cooling, preferably approximately 1 to 5° C.) a medical fluid to a temperature sufficient to slow a metabolic rate of a brain into which the medical fluid is introduced in a matter of seconds (e.g., "quickly", within preferably 2–3 seconds) as it flows through the cryogenic fluid heat exchange apparatus.

Two preferred options are available in which the cryogenic fluid heat exchange apparatus 35 can be used to cool medical fluid, while allowing the medical fluid to be stored at room temperature within the resuscitation apparatus without a docking unit. According to the first option, known as the "on-the-fly" option (shown in FIG. 2a), the cryogenic fluid heat exchange apparatus 35 is used to cool medical fluid to the desired temperature as the medical fluid is being infused into the selected blood vessel. With the second option, known as the "bag-to-bag" option (shown in FIG. 2b), the cryogenic fluid heat exchange apparatus 35 is used to cool medical fluid by passing the medical fluid through the cryogenic fluid heat exchange apparatus between two containers such as medical fluid bags thereby cooling the medical fluid to the desired temperature prior to introducing the medical fluid into the selected blood vessel.

A preferred cryogenic fluid heat exchange apparatus is discussed further with respect to the recirculation option and is disclosed in detail in simultaneously filed co-pending U.S. patent application Ser. No. 09/039,443, now U.S. Pat. No. 6,014,864 (Docket No. WVPB 39257), which is hereby incorporated by reference. Where the cryogenic fluid heat exchange apparatus is used to cool medical fluid prior to infusion, it can replace the third bag of medical fluid.

Figure 2A:
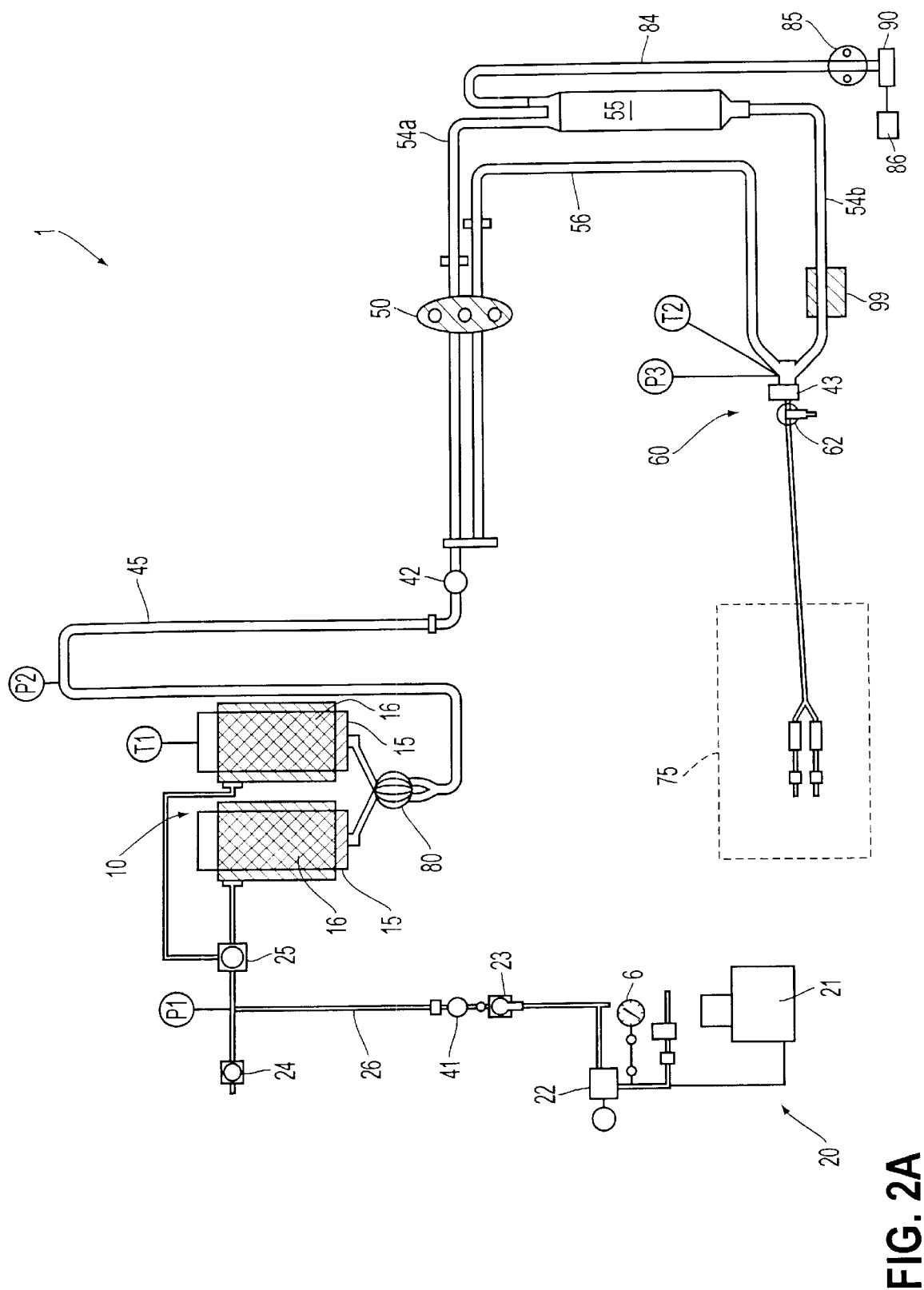
FIG. 2a shows a resuscitation apparatus utilizing a cryogenic fluid heat exchanger apparatus to cool a medical fluid in an "on the fly" position.
Figure 2B:
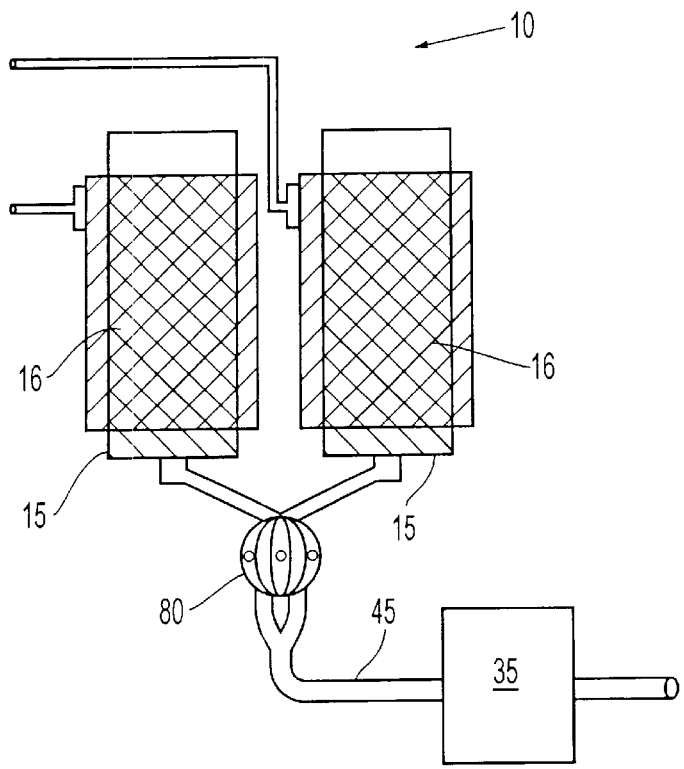
FIG. 2b shows a resuscitation apparatus utilizing a cryogenic fluid heat exchanger apparatus to cool a medical fluid in a "bag-to-bag" position.
Figure 2C:
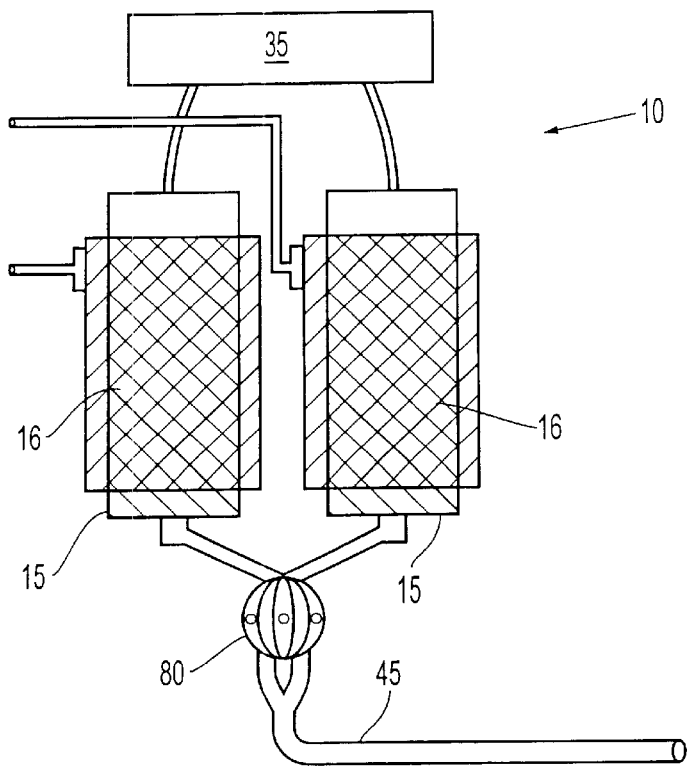
FIG. 2c shows a resuscitation apparatus utilizing a thermoelectric cooling unit to cool medical fluid.
Figure 2D:
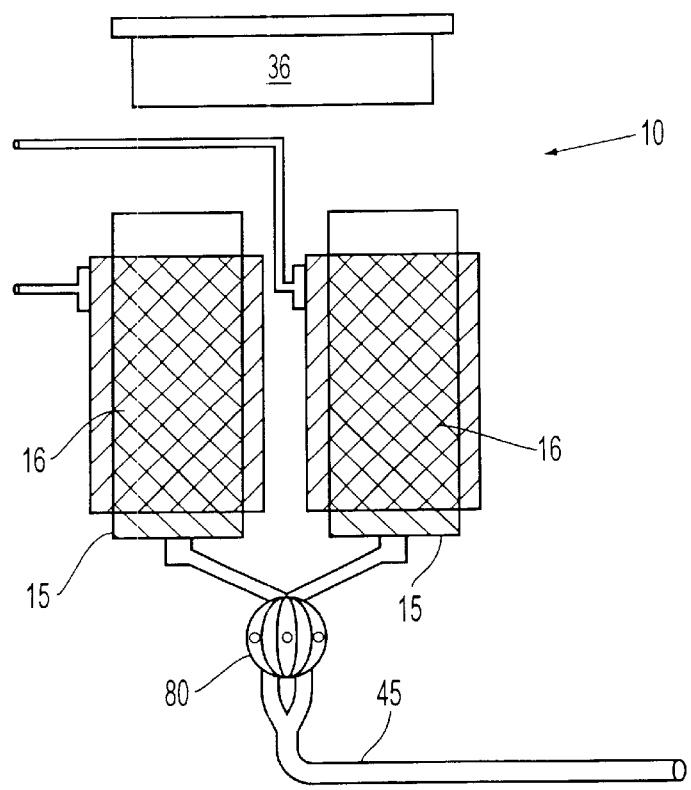
FIG. 2d shows a resuscitation apparatus utilizing a docking apparatus to cool medical fluid.
Figure 2E:
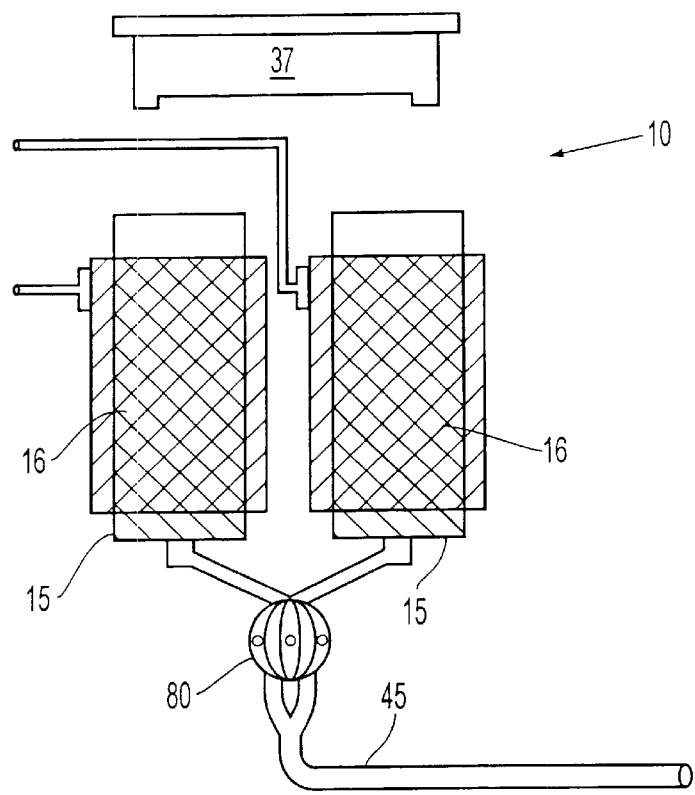
FIG. 2 is a schematic diagram of one embodiment of a resuscitation apparatus according to the invention.

Alternatively, a thermoelectric cooling unit, or TED 36 (shown in FIG. 2c), may be either provided on board or provided as a system in a docking unit 37 (shown in FIG. 2d). The docking module preferably has the ability to maintain three additional liters of medical fluid at appropriate temperatures should additional medical fluid be needed. The docking unit 37 may be powered by, for example, vehicle battery connections or A/C power source connections. The infusion portion of the resuscitation apparatus may be undocked at any time and used within a predetermined time, e.g. 30 minutes, without significant reduction in medical fluid temperature.

The operation of the embodiment of the resuscitation apparatus shown in FIG. 2 will now be discussed.

The catheters 75 for jugular/carotid utilization are placed within the appropriate vessel and back flushed via a syringe. They are then coupled to the catheter interface unit 60, and the catheter interface unit 60 is flushed by activation of valve 62. A purge/flush cycle discussed below removes all air and places cold medical fluid at the catheter entrance.

A similar sequence may be used for femoral aortic arch retroperfusion (AARP) except that after insertion and placement, a balloon at the catheter tip may be inflated via appropriate syringe (i.e., to prevent retro flow into lower extremities). Femoral aortic arch retroperfusion involves insertion of the catheter through the femoral artery up to the aortic artery. Medical fluid is then introduced to the brain via the aortic artery. Arm ligatures or the like may be used to prevent flow to arms.

Upon activation, and preferably also upon release of a safety clamp 80 on the primary infusion tube 45, cold medical fluid flows from the reservoir 10 (or from or through the cryogenic fluid heat exchanger apparatus 35), through control valve 50, circulates down the tube 56 to the catheter interface unit 60 and returns via the tube 54b to the debubbling/flush chamber 55.

The return medical fluid fills the debubbling/flush chamber 55, back flushes tube 54a and overflows into the overflow bag 90. In embodiments, the air/fluid sensor 86 may be included adjacent to the overflow bag 90 to provide a signal until fluid only is present, at which time a change in the signal occurs. The activated air/fluid sensor 86 in turn, through the microprocessor, activates the PERFUSION BUTTON light 3 and, for example, changes or initiates an auditory tone emanating from the air/fluid sensor speaker 4. At this point, the infusion line from the reservoir 10 to the catheter tip is completely free of air bubbles.

On pressing of the PERFUSION BUTTON, control valve 50 switches from the flush mode to the infusion mode. The medical fluid is delivered through the primary infusion tube 45, the tube 54a, the debubbler/flush chamber 55, the tube 54b and subsequently through the catheters 75 at the predetermined rate. The pressure at the catheter tips being monitored by the microprocessor (not shown) via pressure sensor P3 to prevent infusion pressures of greater than 150 mmHg. The inflow flow rate is preferably approximately 500 to 2000 ml/min. Should an excess pressure be observed, the flow rate can be automatically reduced to remain below this value by adjusting the compressor voltage (or the tank valve pressure) or the infusion can be stopped either manually or automatically via safety clamp 80, control valve 50 or valve 62. Temperature sensors T1, T2 at the reservoir 10 and at the catheter interface unit 60 may be used to monitor the temperature of the medical fluid at these points in the perfusion pathway. Further, a flow meter 99 may be provided at a desired point along the perfusate pathway to allow flow characteristics to be monitored.

Figure 3:
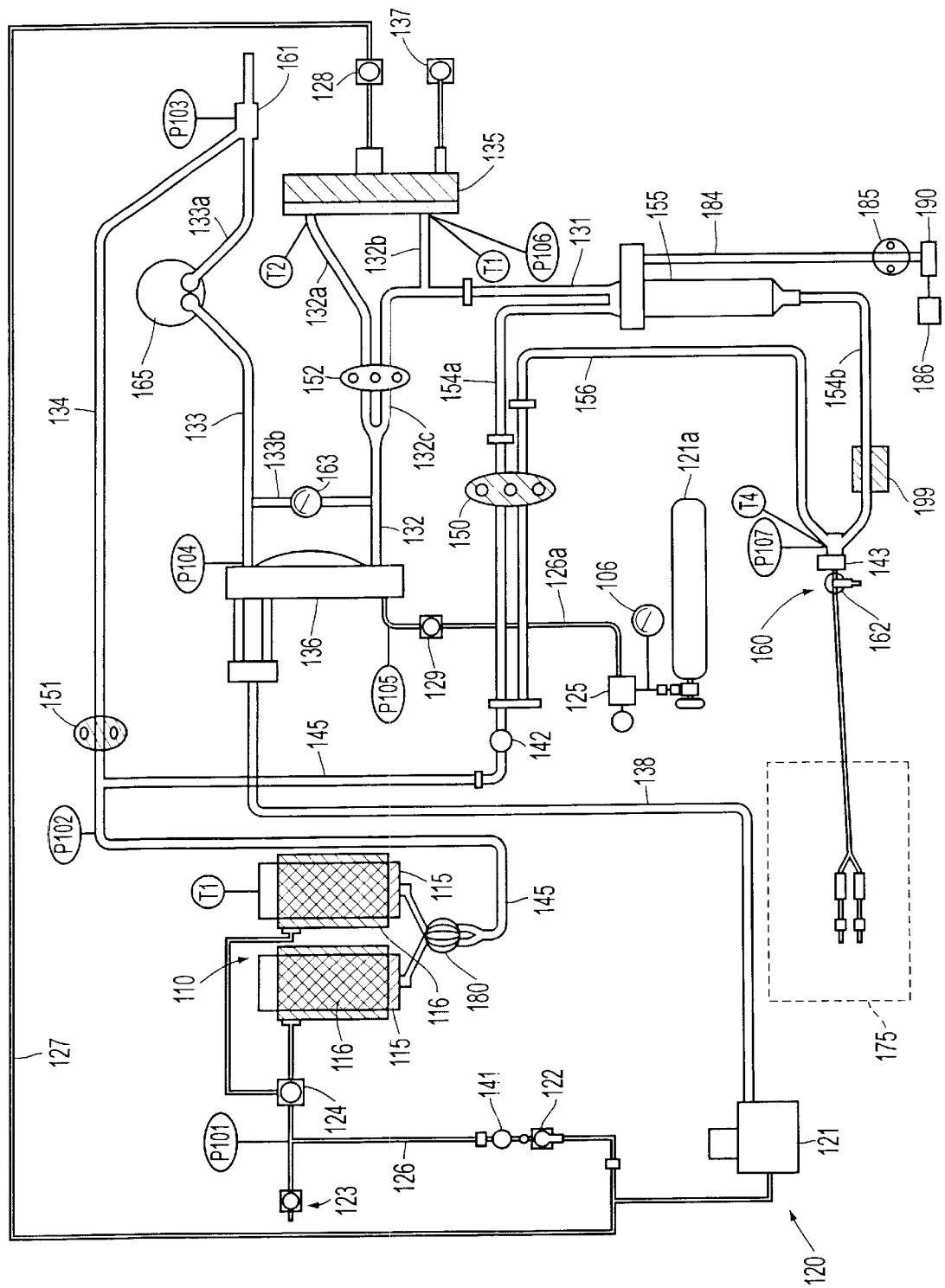
FIG. 3 is a schematic diagram of another embodiment of a resuscitation apparatus according to the invention.
Figure 4:
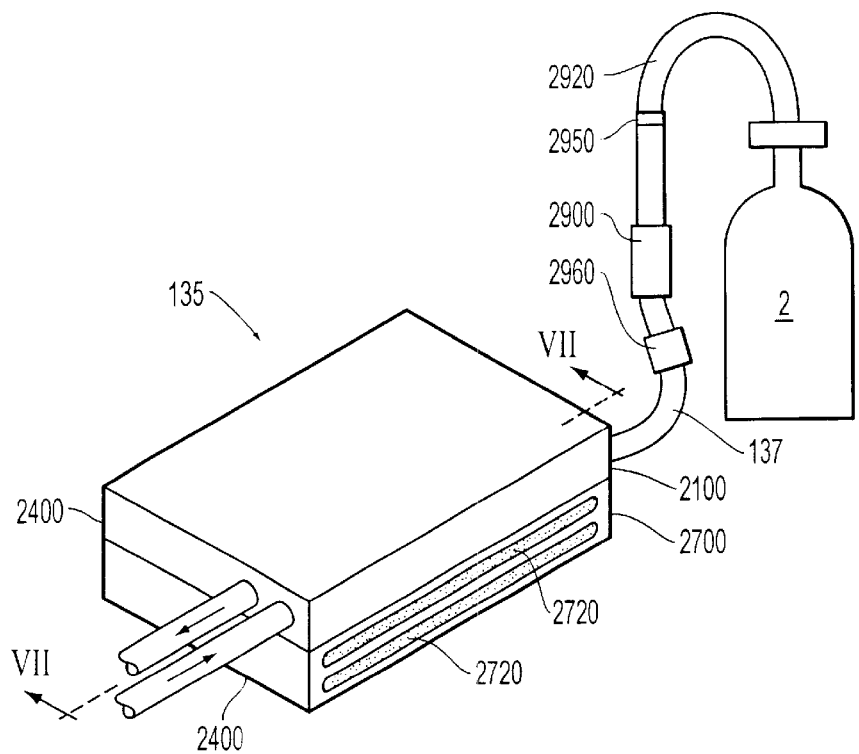
FIG. 4 is a front perspective view of a cryogenic fluid heat exchanger apparatus according to the invention.
Figure 5:
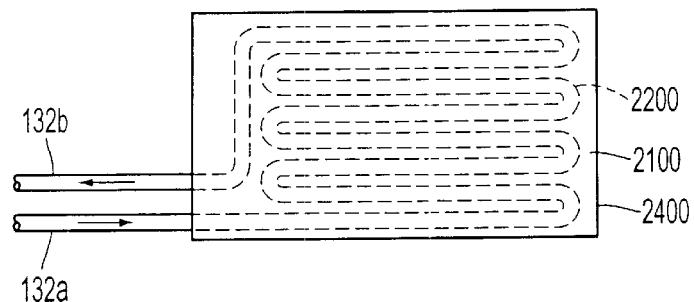
FIG. 5 is a top view of the fluid path component of the apparatus of FIG. 4.
Figure 6:
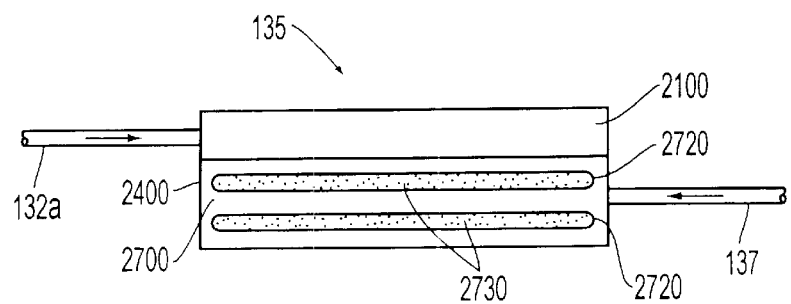
FIG. 6 is a side view of the apparatus of FIG. 4.

Another preferred embodiment of the resuscitation apparatus according to the invention will now be discussed with reference to FIG. 3. This preferred embodiment, hereinafter the recirculation infusion system, or recirculation option, allows blood and/or medical fluid to be withdrawn from a patient, degassed, oxygenated and/or chilled and then reintroduced into the patient. The resuscitation apparatus 100 shown in FIG. 3 is similar to the resuscitation apparatus of FIG. 2. Like reference numbers have been used to represent elements similar to the elements disclosed in FIGS. 1 and 2 and their descriptions have been omitted.

The resuscitation apparatus 100 may employ a cryogenic fluid heat exchange apparatus 135 to chill blood and/or medical fluid to be reintroduced into a patient. The cryogenic fluid heat exchange apparatus 135, is connected to on board compressor 121 via gas tube 127. The cryogenic fluid heat exchange apparatus 135 is also provided with a gas tube 137 for receiving cryogenic fluid therein. Tube 131 runs from the cryogenic fluid heat exchange apparatus 135 to the debubbler/flush chamber 155.

A suitable cryogenic fluid heat exchange apparatus 135 is shown in further detail in FIGS. 4–8. The apparatus 135 includes a fluid path component 2100 and a cryogenic fluid cooling component 2700. The fluid path component 2100 and the cryogenic fluid cooling component 2700 are both housed in a casing 2400, which is preferably formed of a material having low thermal conductivity and high resistivity to low temperature, such as, for example, plastic, plastic composite, wood, carbon epoxy material.

The fluid path component 2100 includes a fluid inlet path, or tube 132a, a fluid outlet path, or tube 132b and a fluid path assembly 2150 disposed therein. The fluid path assembly 2150 includes a fluid path 2200 supported by first and second support plates 2600, 2650. The first support plate 2600 is preferably formed of a material having a low thermal conductivity and high resistivity to low temperature, such as, for example, plastic, plastic composite, wood, carbon epoxy material. The second support plate 2650 is preferably formed of a material having a high thermal conductivity and high resistivity to low temperature, such as, for example, metals such as aluminum, aluminum oxide composite, stainless steel. The fluid path 2200 is preferably tortuous in shape. A tortuous fluid path provides a greater surface area for cooling than, for example, a straight fluid path. The fluid path is preferably 3 to 6 feet in length and formed of a material having high thermal conductivity and high resistivity to low temperature, such as, for example, metals such as aluminum, aluminum oxide, stainless steel. The fluid path can be a separate tube disposed between the support plates or may be formed by walls connecting the support plate. Further, the fluid path may be disposable.

The cryogenic fluid cooling component 2700 includes a cryogenic fluid cooling chamber 2710. The chamber 2710 includes an inner wall 2730 preferably formed of a material having high thermal conductivity and high resistivity to low temperature, such as, for example, metals such as aluminum, aluminum oxide composite, stainless steel. An additional support plate 2730a may also be provided. The chamber 2710 may also include an insert 2800 configured to receive cryogenic fluid from a pressurized cryogenic fluid tank 2910 via a cryogenic fluid inlet path or tube 137 and disperse the cryogenic fluid. The insert 2800 may include holes 2810 configured to direct and disperse cryogenic fluid within the cooling chamber 2710. The holes 2810 are preferably slanted to direct cryogenic fluid onto the inner wall 2730 to facilitate heat transfer from the chamber 2710 to the fluid path component 2100. However, the insert 2800 can be eliminated and the cryogenic fluid introduced directly into the cooling chamber 2710.

The cryogenic fluid inlet path 137 is connected to a cryogenic fluid tank outlet path 2920 by means of a cryogenic fluid conduit coupling device 2900. The coupling device 2900 preferably provides easy coupling of two fluid conduits at very low temperatures without creating a pressure change across the coupling. A suitable coupling device 2900 is discussed in detail in simultaneously filed co-pending application Ser. No. 09/039,378, now U.S. Pat. No. 6,183,019 (Attorney Docket No. WPB 39258), which is hereby incorporated by reference. Pressure relief valves 2950, 2960 are preferably provided on each of the cryogenic fluid inlet path 137 and the cryogenic fluid tank outlet path 2920 to prevent pressure buildup.

The cryogenic fluid is received into the insert 2800 and is dispersed into the chamber 2710, through holes 2810. During injection into the chamber 2710, the cryogenic fluid expands and its temperature drops. In the case of use of liquefied carbon dioxide as the cryogenic fluid, $CO_2$ "snow" may be formed due to the pressure drop. The chamber 2710 may be provided with one or more vents 2720, which may be filtered to allow only gases to escape. For example, in the case of carbon dioxide, the filter holds in the $CO_2$ "snow" while letting gases produced escape. This allows a block of dry ice to form within the chamber. The block of dry ice acts as a secondary source of cooling, in particular when the pressurized cryogenic fluid source is exhausted.

The fluid path assembly 2150 can be moved toward and away from the chamber 2710 by means of a control device 2500 to control the amount of heat exchange between the chamber 2710 and fluid within the fluid path 2200. Temperature sensors 2530 may be provided on a surface of the inner wall 2730 and on one or both of the first and second supports 2600, 2650, or elsewhere. The heat exchange apparatus may be controlled by a microprocessor based on the initial fluid temperature, ambient temperature, desired fluid temperature and desired flow rate. A shunt (not shown) and heater circuit (not shown) may be present in case of sensor or control failure on the support plate 2600 or wall 2730 to re-heat the fluid. Further, temperature sensors T2,T3 can be provided at the fluid entrance and exit to allow the temperature of the fluid at these points to be monitored.

Figure 7:
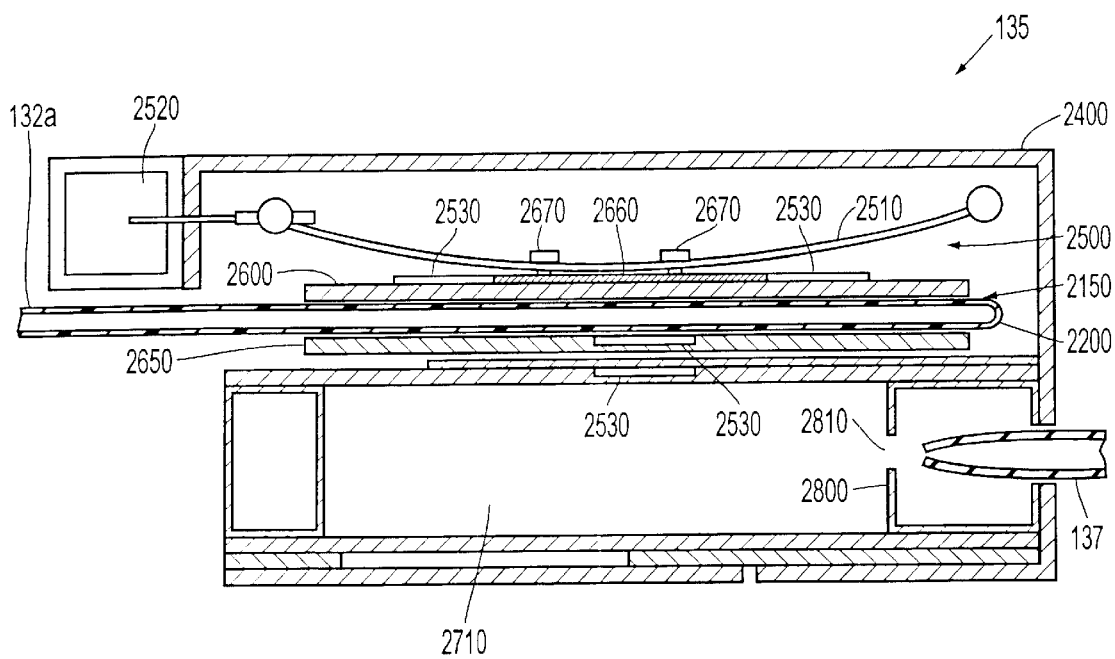
FIG. 7 is a cross-sectional view of the apparatus of FIG. 4 taken along line VII—VII of FIG. 4.
Figure 8:
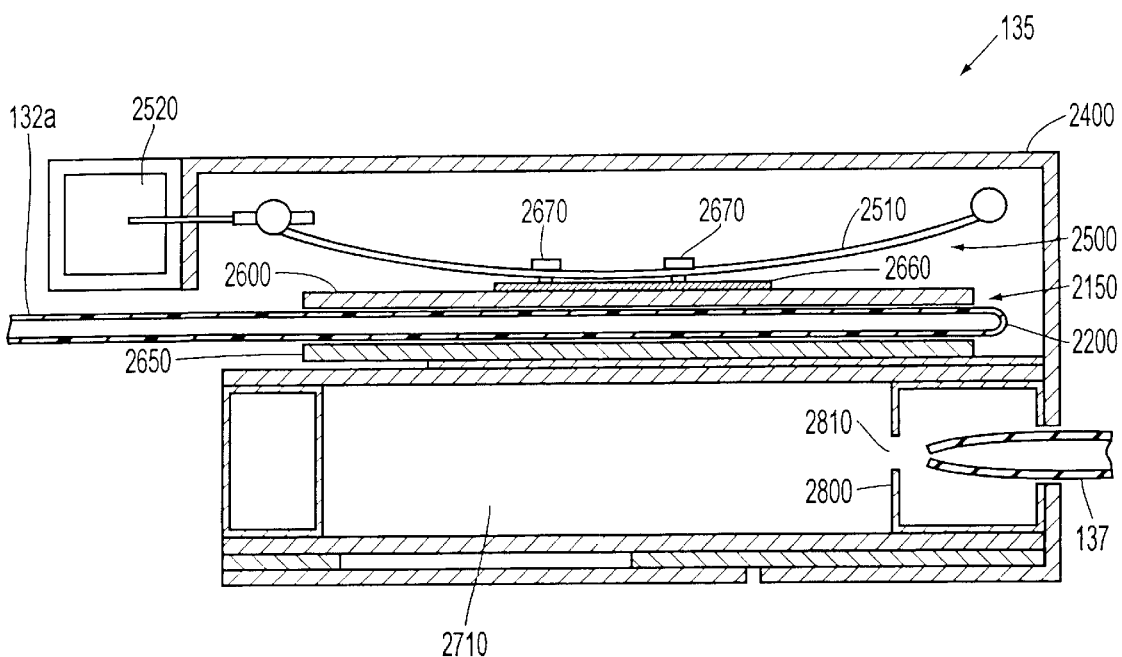
FIG. 8 is a cross-sectional view of the apparatus of FIG. 4 showing the solenoid actuator actuated.

The control device 2500 may include a spring, for example, an arcuate carbon spring 2510, as shown in FIG. 7, attached via screws 2670, 2670 and a connector plate 2660 to the first support plate 2600. Upon actuation of an actuator, for example, a solenoid actuator 2520, the spring 2510 is flexed to force the fluid path assembly 2150 against the chamber 2710. Upon deactuation of the solenoid actuator 2520, the fluid path assembly 2150 is allowed to move away from the chamber 2710.

In operation, blood and/or medical fluid is circulated through the fluid path 2200 via fluid inlet and outlet paths 132a, 132b. Then, a valve on the pressurized cryogenic fluid tank 2910 is opened to start flow of cryogenic fluid. The cryogenic fluid flows through the cryogenic tank fluid outlet path 2920 and the cryogenic fluid inlet path 137. The cryogenic fluid outlet path 2920 and the cryogenic fluid inlet path 137 are connected by the cryogenic fluid conduit coupling device 2900 and are preferably formed of flexible material having excellent properties against high pressure and low temperatures, such as, for example, rubber, polyphosphine tubing, corrugated polytetrafluoroethylene, aluminum coated with hydrophilic urethane coating. The cryogenic fluid flows into the chamber 2710, via the insert 2800, if provided.

Upon actuation of the control device 2500, the fluid path assembly 2150 is pressed against the chamber 2710 to allow heat transfer and cooling of the blood and/or medical fluid circulating through the fluid path 2200. The temperature sensors 2530 sense the temperature being produced at the chamber 2710 and on the first and second support plates 2600, 2650. The sensed temperatures are provided to the microprocessor (not shown) which controls the heat exchange between the chamber 2710 and the blood and/or perfusate by controlling the control device 2500 moving the fluid path assembly 2150 away from the chamber 2710 should the temperature fall below a predetermined parameter, and then returning the tortuous fluid path assembly 2150 to its position adjacent the chamber 2710. Preferably the wall 2730 is maintained at a temperature of approximately 1 to 5° C.

As discussed above with reference to the embodiment of FIG. 2, the cryogenic fluid heat exchange apparatus 135 may also be used to cool the initial medical fluid.

In addition to the cryogenic fluid heat exchange apparatus 135, one or more modules (not shown) containing flexible heat exchange coils surrounded by, e.g., at least one liter of water maintained at between 5° C. and 0.5° C. may be provided. The ability to maintain the water in the frozen state is thermodynamically very useful, but is not mandatory. This variation requires the refrigeration/control unit to be very precise (i.e., ±0.1° C.).

The resuscitation apparatus 100 may further includes a combined pump, filtration, oxygenation and/or debubbler apparatus 136. The combined pump, filtration, oxygenation and/or debubbler apparatus may be disposable and is connected by a tubes 132, 132a to the cryogenic fluid heat exchange apparatus 135 and by a tube 133 to a return pump 165, which is connected by a tube 133a to a return catheter interface unit 161. The tube 134 connects the return catheter interface unit 161 to primary infusion tube 145. A control valve 151 is disposed on tube 134 and a control valve 152 is disposed on the tube 133. Control valve 152 allows bypass of the cryogenic fluid heat exchange apparatus 135 along tube 132c. A valve 163, manually or automatically actuated, may be provided between tubes 132 and 133 to allow bypass of the combined pump, filtration, oxygenation and/or debubbler apparatus along tube 133b upon activation.

A preferred combined pump, filtration, oxygenation and/or debubbler apparatus 136 is described in detail in simultaneously filed co-pending U.S. patent application Ser. No. 09/039,318, now U.S. Pat. No. 6,241,945 (Docket No. WPB 39241), which is hereby incorporated by reference. The apparatus 136 is formed of stackable modules. The apparatus 136 is capable of pumping a fluid through a system as well as oxygenating, filtering and/or debubbling the fluid. The modules are each formed of a plurality of stackable support members and are easily combinable to form a compact apparatus containing desired components. Filtration, oxygenation and/or degassing membranes are disposed between the support members.

Figure 13:
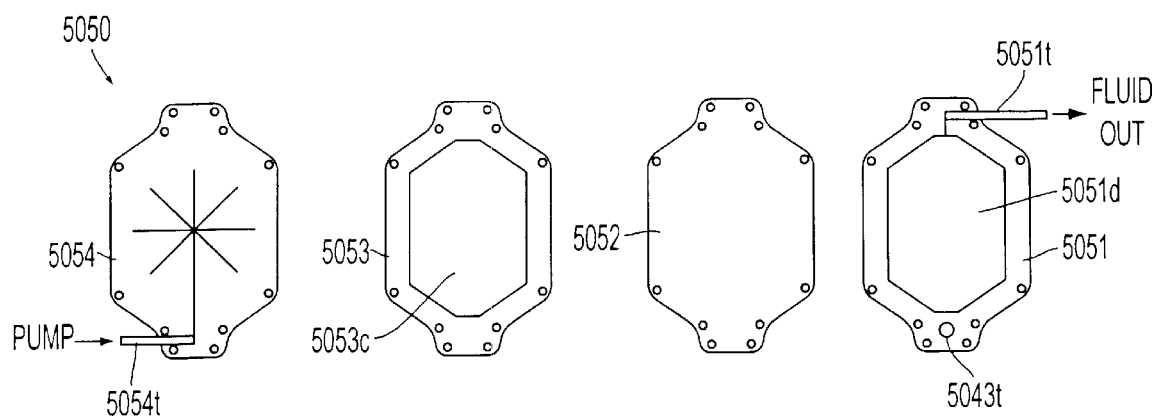
FIG. 13 is an exploded view of a second pump module of a combined pump, filtration, oxygenation and/or debubbler apparatus according to the invention.
Figure 14:
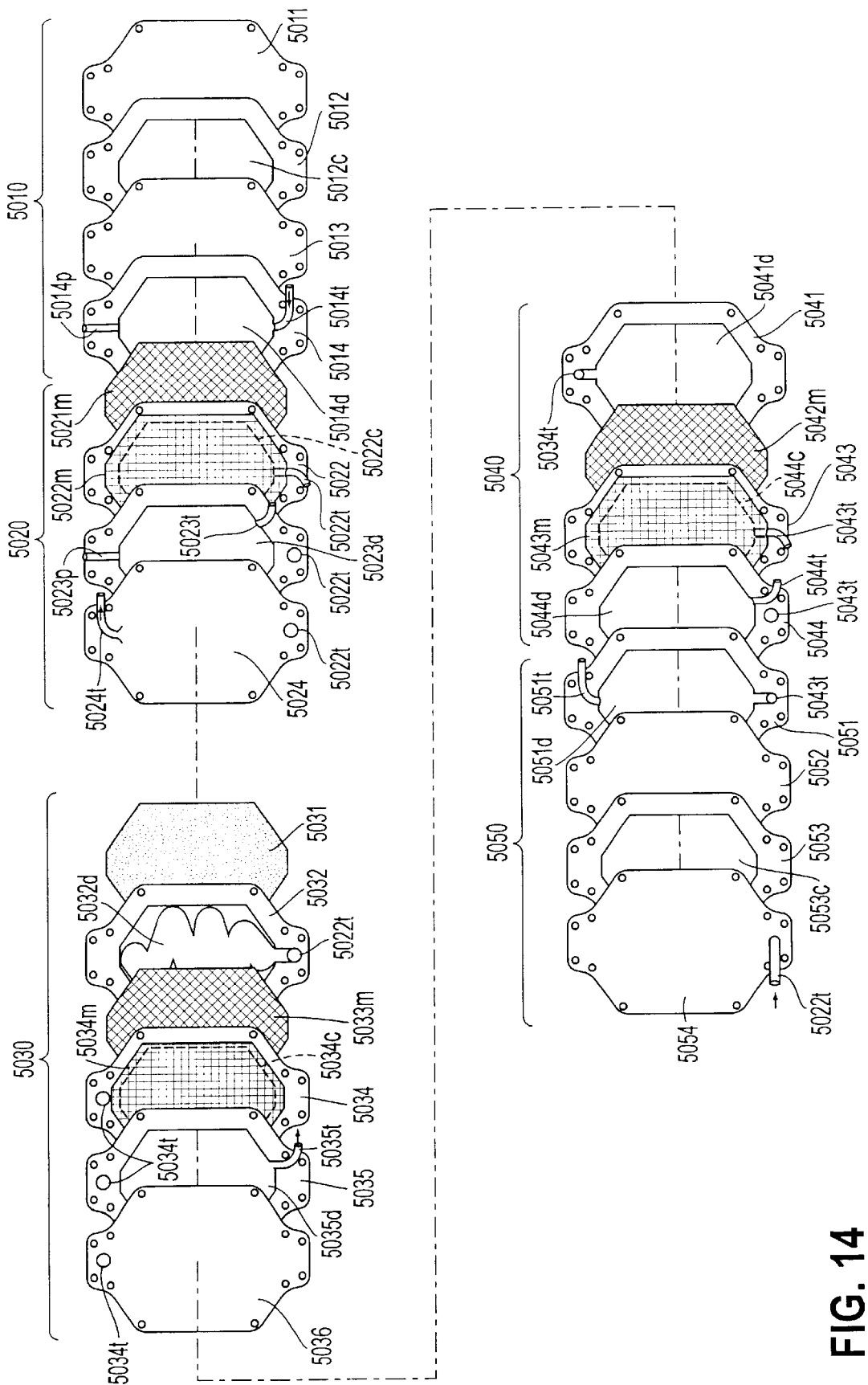
FIG. 14 is an exploded perspective view showing the modules of FIGS. 9–13 assembled together.
Figure 15:
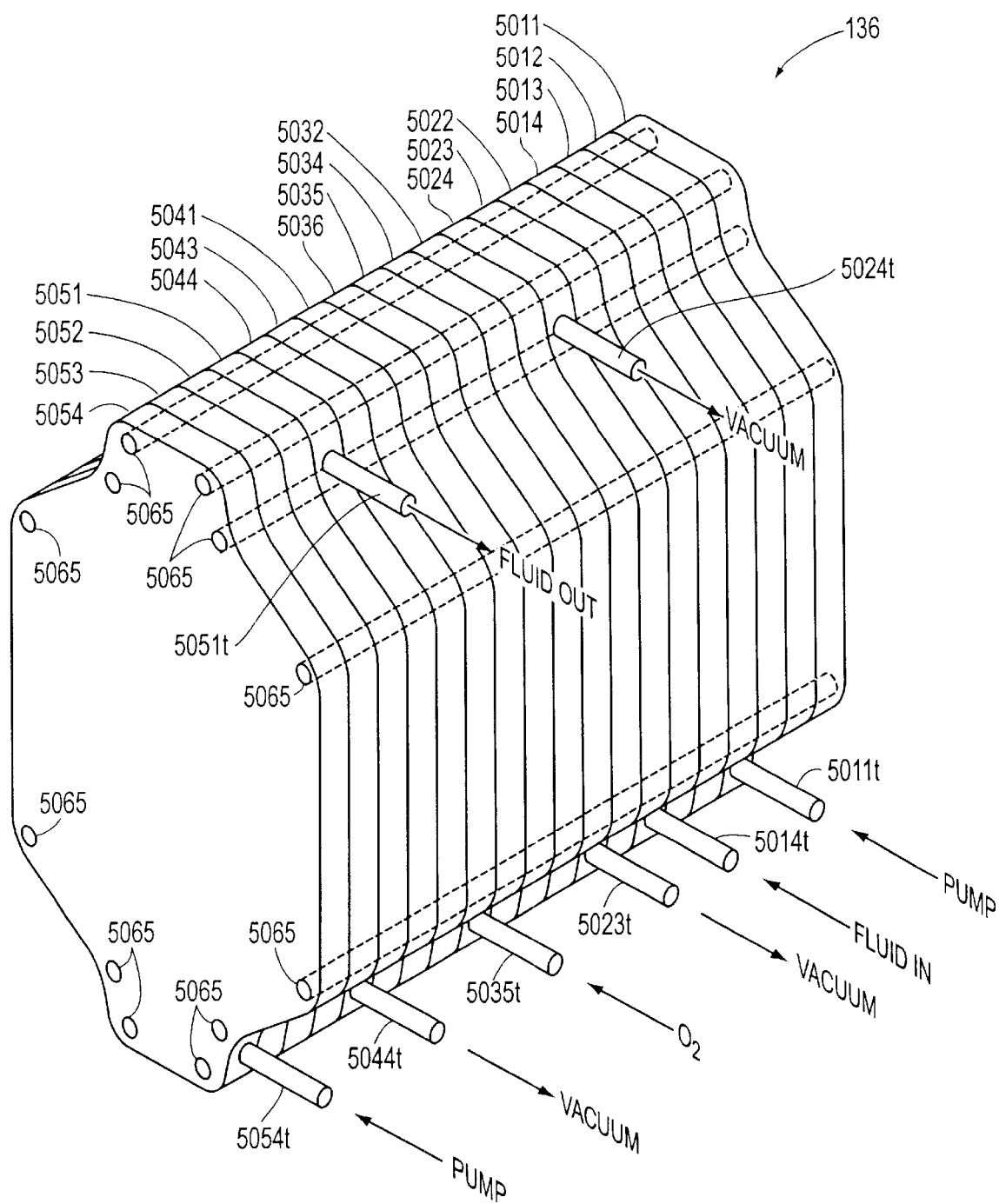
FIG. 15 is a front perspective view of an assembled of a modular combined pump, filtration, oxygenation and/or debubbler apparatus according to the invention.

FIGS. 9–13 show various modules that may be stacked to form a combined pump, filtration, oxygenation and/or debubbler apparatus, such as the combined pump, filtration, oxygenation and debubbler apparatus 5001 shown in FIGS. 14–15. As depicted in these figures, the combined pump, filtration, oxygenation and debubbler apparatus 5001 is preferably formed of a plurality of stackable support members groupable to form one or more modules.

Interposed between the plurality of stackable support member are filtration, oxygenation and/or degassing membranes depending on a particular user's needs. The filtration, oxygenation and/or degassing membranes are preferably commercially available macro-reticular hydrophobic polymer membranes hydrophilically grafted in a commercially known way, such as, for example, ethoxylation, to prevent protein deprivation, enhance biocompatibility with, for example, blood and to reduce clotting tendencies. The filtration membrane(s) is preferably hydrophilically grafted all the way through and preferably has a porosity (pore size) within a range of 15 to $35\mu$, more preferably 20 to $30\mu$, to filter debris in a fluid, preferably without filtering out cellular or molecular components of the fluid. The degassing membrane(s) and oxygenation membrane(s) are hydrophilically surface treated to maintain a liquid-gas boundary. The degassing membrane(s) and oxygenation membrane(s) preferably have a porosity of $15\mu$ or less, more preferably $10\mu$ or less.

Figure 9:
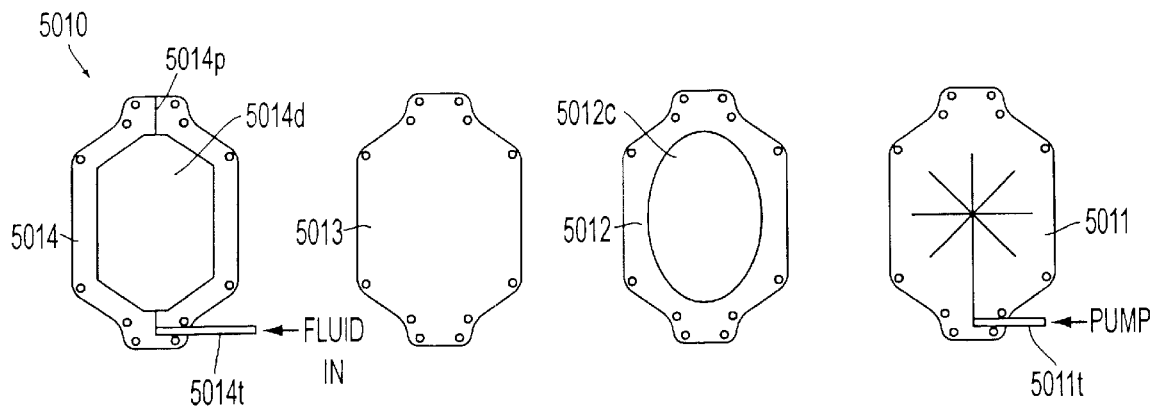
FIG. 9 is an exploded view of a first pump module of a combined pump, filtration, oxygenation and/or debubbler apparatus according to the invention.
Figure 10:
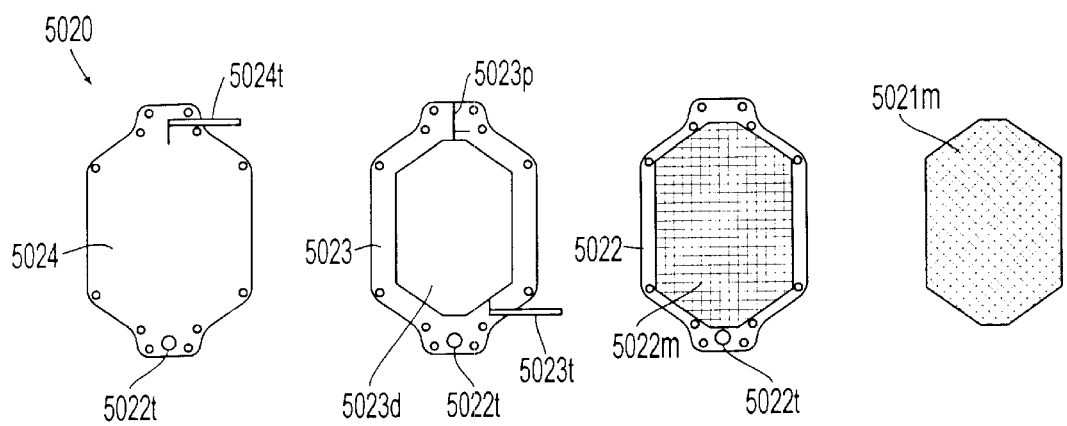
FIG. 10 is an exploded view of a filtration module of a combined pump, filtration, oxygenation and/or debubbler apparatus according to the invention.

The modules may include a first pump module 5010, as shown in exploded view in FIG. 9; a filtration module 5020, as shown in exploded view in FIG. 10; an oxygenation module 5030, as shown in exploded view in FIG. 11; a debubbler module 5040, as shown in exploded view in FIG. 12; and a second pump module 5050, as shown in exploded view in FIG. 13. The pump modules are each connected to a source of pump fluid and are actuated either manually or by the microprocessor. The support members are preferably similarly shaped. For example, the support members may each be plate-shaped; however, other shapes may also be appropriate. As shown in FIG. 15, the support members are preferably removably connected by screws or bolts 5065; however, other fasteners for assembling the apparatus may also be appropriate.

The first pump module 5010 preferably includes a first (end) support member 5011, a second support member 5012 with a cut-out center area 5012c, a diaphragm 5013 and a third support member 5014. The support members of this module and each of the other modules are preferably thin and substantially flat (platelike), and can be formed of any appropriate material with adequate rigidity and preferably also biocompatibility. For example, various resins and metals may be acceptable. A preferred material is an acrylic/polycarbonate resin.

The first (end) support member 5011 is preferably solid and provides support for the pump module 5010. The first (end) support member 5011 preferably includes a domed-out cavity for receiving pump fluid such as air. Tubing 501 it is provided to allow the pump fluid to enter the pump module 5010. The diaphragm 5013 may be made of any suitable elastic and preferably biocompatible material, and is preferably polyurethane. The third support member 5014 includes a domed-out fluid cavity 5014d and tubing 5014t for receiving fluid, such as, for example, blood or an artificial perfusate, into the cavity 5014d of the pump module 5010. The first pump module, or any of the other modules, may also include a port 5014p for sensors or the like. Preferably hemocompatible anti-backflow valves serve to allow unidirectional flow through the pump module 5010.

The filtration module 5020 preferably includes a filtration membrane 5021m which forms a boundary of cavity 5014d, a first support member 5022 with a cut-out center area 5022c, a degassing membrane 5022m and second and third support members 5023 and 5024. The filtration membrane 5021m is preferably a $25\mu$ macro-reticular filtration membrane modified to enhance biocompatibility with, for example, blood and to reduce clotting tendencies (like the other supports, filters and membranes in the device). The degassing membrane 5022m is preferably a $0.2-3\mu$ macro-reticular degassing membrane with a reverse flow aqueous pressure differential of at least 100 mmHg for $CO_2$ removal surface modified to enhance biocompatibility.

The first support 5022 includes tubing 22t for forwarding fluid into the oxygenation module 30, or another adjacent module, if applicable, after it has passed through the filtration membrane 5021m and along the degassing membrane 5022m. The second support member 5023 of the filtration module 5020 includes a domed-out fluid cavity 5023d and tubing 5023t through which a vacuum may be applied to the cavity 5023d to draw gas out of the fluid through degassing membrane 5022m. The fourth support member 5024 is preferably solid and provides support for the filtration module 5020. The third support member can also include tubing 5024t through which a vacuum may be applied to draw gas out of the fluid through the degassing membrane 5031m of the oxygenation module 5030 as discussed below. The filtration module 5020, or any of the other modules, may also include a port 5023p for sensors or the like.

The oxygenation module 5030 includes a degassing membrane 5031m, a first support member 5032, a filtration membrane 5033m, an oxygenation membrane 5034m, a second support member 5034 with a cut-out center area 5034c, and third and fourth support members 5035, 5036. The degassing membrane 5031m is preferably a 0.2–3µ macro-reticular degassing membrane with a reverse flow aqueous pressure differential of at least 100 mmHg surface modified to enhance biocompatibility.

The first support member 5032 includes a domed-out fluid cavity 5032d. The surface of the domed-out fluid cavity 5032d preferably forms a tortuous path for the fluid, which enhances the oxygenation and degassing of the fluid. The filtration membrane 5033m is preferably a 25µ macro-reticular filtration membrane modified to enhance biocompatibility. The oxygenation membrane 5034m is preferably a 0.2–1µ macro-reticular oxygenation membrane with a reverse flow aqueous pressure differential of at least 100 mmHg surface modified to enhance biocompatibility.

The second support member 5034 includes tubing 5034t for forwarding fluid out of the oxygenation module 5030 into the debubbler module 5040, or another adjacent module, if applicable. The third support member 5035 includes a domed-out cavity 5035d and tubing 5035t for receiving oxygen from an external source. The fourth support member 5036 is preferably solid and provides support for the oxygenation module 5030.

The debubbler module 5040 includes a first support member 5041, a filtration membrane 5042m, a degassing membrane 5043m, a second support member 5043 having a cut-out center area 5043c, and a third support member 5044. The first support member 5041 has a domed-out fluid cavity 5041d.

The filtration membrane 5042m is preferably a 25µ macro-reticular filtration membrane modified to enhance biocompatibility. The degassing membrane 5043m is preferably a 0.2–3µ macro-reticular degassing membrane with a reverse flow aqueous pressure differential of at least 100 mmHg surface modified to enhance biocompatibility. The second support member 5043 has tubing 5043t for forwarding fluid out of the debubbler module 5040 into the pump module 5050, or another adjacent module, if applicable. The third support member 5044 includes a domed-out cavity 5044d and tubing 5044t through which a vacuum may be applied to draw gas out of the fluid through the degassing membrane 5043m.

The second pump module 5050 may correspond to the first pump module 5010. It preferably includes a first support member 5051, a diaphragm 5052, a second support member 5053 with a cut-out center area 5053c, and a third (end) support member 5054. The first support member 5051 includes a domed out fluid cavity 5051d and tubing 5051t for allowing fluid to exit the pump module. The diaphragm 5052 is preferably a polyurethane bladder.

The third (end) support piece member 5054 is preferably solid and provides support for the pump module 5050. Support member 5054 preferably includes a domed out cavity (not shown) for receiving pump fluid. Tubing 5054a is provided to allow the pump fluid such as air to enter the pump module 5050. Preferably hemocompatible anti-backflow valves may serve to allow unidirectional flow through the pump module 5050.

In operation, blood and/or medical fluid enters the first pump module 5010 through tube 5014t passes through the filtration membrane 5021m and along the degassing membrane 5022m. A small vacuum is applied through tubing 5023t to draw gas through the degassing membrane 5022m. Next, the blood and/or medical fluid travels into the oxygenation module 5030 via internal tubing 5022t, passing along the degassing membrane 5031m, through the filtration membrane 5033m and along the oxygenation membrane 5034m. Oxygen is received into the domed-out cavity 5035d of the third support member of the oxygenation module 5030 via tubing 5035t and passes through the oxygenation membrane 5034m into the blood and/or medical fluid as the blood and/or medical fluid travels along its surface.

After being oxygenated by the oxygenation module 5030, the blood and/or medical fluid then travels via internal tubing 5034t into the debubbler module 5040. The blood and/or medical fluid passes through the filtration membrane 5042m and along the degassing membrane 5043m. A small vacuum force is applied through tubing 5044t to draw gas out of the blood and/or medical fluid through the degassing membrane 5043m. After passing through the degassing module 5040, the blood and/or medical fluid travels into the second pump module 5050 through tubing 5054t, and exits the second pump module 5050 via tubing 5051t.

The combined pump, filtration, oxygenation and/or debubbler apparatus 136 is attached to the onboard compressor 121 via a vacuum tube 138 and to an oxygen tank 121a via the gas tube 126a, which has two gas valves 125,129 disposed thereon. The combined pump, filtration, oxygenation and/or debubbler apparatus 136 may also be used to augment flow on the return. Further, the combined pump, filtration, oxygenation and/or debubbler apparatus allows the minimization of dead volume and polymer-to-blood contact.

Any suitable pumping device, for example, a pulsatile or rotary, pneumatically, hydraulically or electrically actuated device with appropriate valves may replace the pump modules 5010, 5050 discussed above. Alternatively, the filtration, oxygenation and debubbler modules 5020, 5030 and 5040 previously described may be used without the pump modules 5010, 5050, or in various combinations. As shown in FIG. 3, return pump 165 may be used in addition to the combined pump, filtration, oxygenation and/or debubbler apparatus with one of the pump modules acting as a variable volume compensation chamber/module. Further, various other filtration, oxygenation (for example, a JOSTRA™ oxygenator) and/or debubbler apparatus may replace the modules discussed above.

The operation of the embodiment of the resuscitation apparatus shown in FIG. 3 will now be discussed.

The recirculation option procedure begins with a direct infusion of a pre-determined amount of medical fluid to be delivered to the mammal, at a given flow rate and maximal infusion pressure, via an appropriate blood vessel. The preferred vessels include the jugular vein and carotid artery—standard or retroflow. Specific catheters 175 are employed based on the entry site. The perfusion rate should be sufficient (e.g., 1–3 liter/min) to allow a systemic venous pressure to be achieved (preferably approximately 50 mmHg or greater). This allows a suitable venous return to provide a self sustaining recirculation to be achieved. The outflow rate is preferably approximately 500 to 2000 ml/min and is preferably maintained at a temperature within a range of approximately 20–37° C. (i.e., an approximately 15° temperature differential @ 2000 ml/min). It is preferable that the maximum transmembrane pressure be within a range of approximately 50 to 80 mmHg, that the maximum oxygen flow rate be approximately 3.0 liters/min and that the total priming volume be approximately 350 ml return temperature. The apparatus can also be utilized with children or small mammals with the pressure and flow rate modified accordingly. For example, with adults the inflow rate is preferably approximately 500 to 6000 ml/min. with a pressure of no greater than 150 mm Hg while for children the inflow rate is preferably approximately 500 to 2000 ml/min. with a pressure no greater than 150 mm Hg. However, the flow rate and pressure will depend on the particular organ and its size.

First, the additional return catheter assembly (not shown) connected to a return catheter interface unit 161 is placed in the femoral vein and, as with the embodiment of FIG. 2, the catheters 175 for jugular/carotid utilization are placed within the appropriate vessel and back flushed via a syringe. Catheters 175 are then coupled to the catheter interface unit 160, and the interface unit 160 is flushed by actuation of valve 162. The purge/flush cycle discussed below removes all air and places cold perfusate at the catheter entrance.

Upon activation, and preferably also release of a clamp 180 on the primary infusion tube 145, medical fluid flows from the reservoir 110, through the control valve 151, along the tube 134, through the return catheter interface unit 161, along the tube 133a, through the pump 165, along the tube 133, through the combined pump, filtration, oxygenation and/or debubbler apparatus 136, along the tubes 132, 132a, through the cryogenic fluid heat exchange apparatus 135, along tubes 132b, 131 to the debubbling/flush chamber 155, pressurizing the components and eliminating air bubbles in that portion of the apparatus. Once the combined pump, filtration, oxygenation and/or debubbler apparatus 136 and cryogenic fluid heat exchange apparatus 135 are pressurized, the medical fluid is routed by control valve 151 down the primary infusion tube 145 and tube 156, through control valve 150, to the catheter interface unit 160 and returns via tube 154b to the debubbling/flush chamber 155. As previously discussed, an air/fluid sensor 186 may be included to provide a signal until fluid only is present, at which time a continuous sound occurs.

The return medical fluid fills the debubbling/flush chamber 155, back flushes tube 154a and overflows into the overflow bag 190, activating the air/fluid sensor 186 which, in turn, through the microprocessor activates the PERFUSION BUTTON light 103 and, for example, changes an auditory tone emanating from the air/fluid sensor speaker 104.

On pressing of the PERFUSION BUTTON 102, control valve 150 switches from the flush mode to infusion mode. The medical fluid is delivered through the primary infusion tube 145, the tube 154a, the debubbling/flush chamber 155, the tube 154b and subsequently through the catheters 175 at the predetermined rate with the pressure at the catheter tips being monitored by the microprocessor (not shown) via pressure sensor P107 to prevent infusion pressures of greater than 150 mmHg. Should excess pressure be observed, the flow rate can be automatically reduced to remain below this value by adjusting the compressor voltage (or the tank valve pressure) or the infusion can be stopped either manually or automatically via safety valve 180, control valve 150 or valve 162. Additional pressure sensors P101–P106 are provided in the gas and perfusion circuits to allow monitoring of the pressure respectively therein. Temperature sensors T1,T2,T3,T4 are provided at the reservoir 110, the inlet and outlet fluid paths of the cryogenic fluid heat exchange apparatus, as discussed previously, and the catheter interface unit 160 to allow monitoring of the temperature of the perfusate at these points in the perfusion circuit.

The return catheter (not shown) which was previously placed in the femoral vein, flushed and attached to the return catheter interface unit 161, is allowed to fill during the active infusion period (i.e., ~1 min.). The rate of recirculation is a function of the minimal fill time of the return pump 165. The return blood and/or medical fluid is mildly heparinized and mixed with additional medical fluid via tube 134 prior to direct entry into the combined pump, filtration, oxygenation and/or debubbler apparatus 136. After oxygenation/degassing, the blood and/or medical fluid is transferred into the variable volume compensation/pumping chamber of combined pump, filtration, oxygenation and/or debubbler apparatus 136, through tubes 132 and 132a, the cryogenic fluid heat exchange apparatus 135, the tube 131, the debubbling/flush chamber 155, the tube 154b and then into the patient through the catheter 175.

In the aortic arch perfusion mode significant medical fluid may be supplied to the coronary arteries as well as up to the brain.

While the invention has been described in conjunction with specific embodiments thereof, it is evident that many alternatives, modifications and variations may be apparent to those skilled in the art. Accordingly, the preferred embodiments of the invention as set forth herein is intended to be illustrative, not limiting. Various changes may be made without departing from the spirit and scope of the invention as defined in the following claims.

What is claimed is:

1. A resuscitation apparatus, comprising:
    a fluid pathway in fluid communication with a source of medical fluid;
    an interface unit for attaching the fluid pathway to the cardiovascular system of a mammal suffering from impaired blood flow in order to establish an artificial circulation in the mammal utilizing the medical fluid; and
    heat exchange apparatus in the fluid pathway that provides intense cooling to quickly chill the medical fluid a sufficient amount to slow a metabolic rate of an organ of a mammal into which the medical fluid is introduced.

2. The apparatus according to claim 1, wherein the source of medical fluid is a reservoir in fluid communication with the fluid pathway.

3. The apparatus according to claim 2, further comprising a pressure source for pressurizing the medical fluid within the reservoir.

4. The apparatus of claim 3, wherein the reservoir comprises at least one bag of medical fluid and the pressure source comprises a compressor in fluid communication with a pressure cuff disposed around said bag.

5. The apparatus of claim 3, wherein the reservoir comprises at least one bag of medical fluid and the pressure source comprises a compressed gas tank in fluid communication with a pressure cuff disposed around said bag.

6. The apparatus of claim 1, wherein the heat exchange apparatus utilizes expansion of a cryogenic fluid in a non-recirculating expansion chamber to chill the medical fluid.

7. The apparatus according to claim 6, wherein the chamber includes at least one wall formed of a material having high thermal conductivity and high resistivity to low temperature, and the heat exchange apparatus further comprises a fluid path assembly adjacent the chamber for circulating therethrough the medical fluid.

8. The apparatus of claim 1, comprising at least two containers, the heat exchange apparatus comprising a cryogenic fluid heat exchange apparatus between and in fluid communication with both of said containers to permit chilling of the medical fluid through the cryogenic fluid heat exchange apparatus as the medical fluid is passed back and forth between the at least two containers prior to introducing the medical fluid into the fluid pathway.

9. The apparatus of claim 1, further comprising a control valve within the fluid pathway which is shiftable between a position in which medical fluid flows through the fluid pathway to prime the fluid pathway and a position in which the medical fluid is directed through the fluid pathway to the interface unit to be introduced into a mammal.

10. The apparatus of claim 1, further comprising a recirculation fluid pathway in fluid communication with the fluid pathway, and a recirculation interface unit for attaching the recirculation fluid pathway to a blood vessel of the mammal.

11. The apparatus of claim 10, further comprising a recirculation pump, a recirculation heat exchange apparatus and a combined pump filtration, oxygenation and/or debubbler apparatus in fluid communication with the recirculation fluid pathway.

12. The apparatus according to claim 11, wherein the recirculation heat exchange apparatus utilizes expansion of a compressed cryogenic fluid in a non-recirculating expansion chamber to chill the medical fluid.

13. The apparatus according to claim 12, wherein the chamber includes at least one wall formed of a material having high thermal conductivity and high resistivity to low temperature; and the recirculation heat exchange apparatus further comprises a fluid path assembly adjacent the chamber for circulating therethrough medical fluid.

14. The apparatus of claim 11, wherein the combined pump filtration, oxygenation and/or debubbler apparatus comprises a plurality of stackable support members assembled to form one or more modules, each module capable of one of pumping, filtering, oxygenating and debubbling a fluid.

15. The apparatus of claim 14, wherein the modules comprise a filtration module, an oxygenation module, a debubbler module and one or more pump modules.

16. The apparatus of claim 10, further comprising a control valve which is shiftable between a position in which medical fluid is diverted from the fluid pathway into the recirculation fluid pathway to prime the recirculation fluid pathway, and a position in which medical fluid is blocked from passing directly from the fluid pathway into the recirculation fluid pathway.

17. The apparatus of claim 1, wherein the resuscitation apparatus is portable.

18. A portable resuscitation apparatus, comprising:
a portable casing;
a reservoir disposed within the portable casing for holding therein a medical fluid;
a fluid pathway disposed within the portable casing and in fluid communication with the reservoir;
an interface unit for attaching the fluid pathway to the cardiovascular system of a mammal suffering from impaired blood flow in order to establish an artificial circulation in said mammal; and
docking apparatus that allows the portable resuscitation apparatus to be removably attached to a heat exchange apparatus in order to maintain the medical fluid within the reservoir chilled an amount sufficient to slow a metabolic rate of an organ of a mammal into which the medical fluid is introduced until the portable resuscitation apparatus is needed.

19. The apparatus of claim 18, wherein the heat exchange apparatus comprises a thermoelectric device.

20. A portable resuscitation apparatus, comprising:
a portable casing;
a reservoir disposed within the portable casing for holding therein a medical fluid;
a fluid pathway at least partially disposed within the portable casing and in fluid communication with the reservoir;
an interface unit for attaching the fluid pathway to the cardiovascular system of a mammal suffering from impaired blood flow in order to establish an artificial circulation in said mammal;
heat exchanger apparatus in fluid communication with the reservoir for chilling medical fluid within the reservoir a sufficient amount to slow a metabolic rate of an organ of a mammal into which the medical fluid is introduced; and
a control unit that controls the introduction of medical fluid from the reservoir into the fluid pathway to prime the fluid pathway prior to allowing fluid communication between the fluid pathway and the interface unit.

21. A method of reducing anoxic and/or ischemic injury in a mammal suffering from impaired blood flow, comprising:
utilizing heat exchange apparatus that provides intense cooling to quickly chill a medical fluid a sufficient amount to slow a metabolic rate of an organ of a mammal into which the medical fluid is introduced; and
introducing the chilled medical fluid into the cardiovascular system of a mammal suffering from impaired blood flow in order to establish an artificial circulation in the mammal, whereby said organ remains substantially intact.

22. The method of claim 21, further comprising introducing the medical fluid into the cardiovascular system from a pressurized reservoir.

23. The method of claim 22, comprising pressurizing the reservoir by activating a pressure cuff surrounding the reservoir.

24. The method of claim 21, further comprising passing the medical fluid back and forth between at least two containers of reservoir through the heat exchange apparatus to chill the medical fluid a sufficient amount to slow a metabolic rate of the organ of a mammal prior to introducing the chilled medical fluid into said cardiovascular system.

25. The method of claim 24, wherein the heat exchange apparatus utilizes expansion of a cryogenic fluid in a non-recirculating expansion chamber to chill the medical fluid.

26. The method of claim 21, further comprising:
withdrawing medical fluid from the mammal;
circulating the withdrawn medical fluid through said heat exchange apparatus; and
reintroducing the medical fluid into the mammal.

27. The method of claim 26, further comprising:
providing a recirculation pump and a recirculation heat exchange apparatus in fluid communication with the recirculation fluid pathway; and
passing the medical fluid withdrawn from the mammal through the recirculation heat exchange apparatus in order to chill the medical fluid a sufficient amount to slow a metabolic rate of the organ of a mammal.

28. The method of claim 26, further comprising:
oxygenating and degassing the medical fluid withdrawn from the mammal prior to reintroducing the medical fluid into the mammal.

29. The method of claim 21, wherein said organ of a mammal is a brain, said brain remaining substantially neurologically intact.

30. A method of reducing anoxic and/or ischemic injury in a mammal suffering from impaired blood flow, comprising:

removably attaching a portable resuscitation apparatus to a heat exchange apparatus in order to maintain medical fluid within said apparatus chilled a sufficient amount to slow a metabolic rate of an organ of a mammal into which the medical fluid is introduced;

detaching the portable resuscitation apparatus from said heat exchange apparatus; and introducing chilled medical fluid from the detached portable resuscitation apparatus into the cardiovascular system of a mammal suffering from impaired blood flow in order to establish an artificial circulation in the mammal utilizing the medical fluid.

31. The method of claim 30, wherein the portable resuscitation apparatus comprises a medical fluid reservoir, a fluid pathway in fluid communication with the reservoir and an interface unit for attaching the fluid pathway to the cardiovascular system of a mammal; and said method further comprises:

introducing chilled medical fluid from the reservoir into the fluid pathway to prime the fluid pathway prior to allowing fluid communication between the fluid pathway and the interface unit to introduce chilled medical fluid from the detached portable resuscitation apparatus into the cardiovascular system of said mammal.

32. The method of claim 30, wherein said organ of a mammal is a brain.

33. An apparatus for reducing anoxic and/or ischemic injury in a mammal suffering from impaired blood flow, comprising:

heat exchange means for providing intense cooling to quickly chill a medical fluid a sufficient amount to slow a metabolic rate of an organ of a mammal into which the medical fluid is introduced; and fluid introduction means for introducing the chilled medical fluid into the cardiovascular system of a mammal suffering from impaired blood flow in order to establish an artificial circulation in the mammal, whereby said organ remains substantially intact.

34. The apparatus of claim 33, wherein the apparatus is portable.

35. The method of claim 33, wherein said organ of a mammal is a brain, said brain remaining substantially neurologically intact.

36. An apparatus for reducing anoxic and/or ischemic injury in a mammal suffering from impaired blood flow, comprising:

attaching means for removably attaching a portable resuscitation apparatus to a heat exchange apparatus in order to maintain medical fluid within said apparatus chilled a sufficient amount to slow a metabolic rate of an organ of a mammal into which the medical fluid is introduced;

detachment means for detaching the portable resuscitation apparatus from the heat exchange apparatus; and fluid introduction means for introducing chilled medical fluid from the detached portable resuscitation apparatus into the cardiovascular system of a mammal suffering from impaired blood flow in order to establish an artificial circulation in the mammal utilizing the medical fluid.

37. The method of claim 36, wherein said organ of a mammal is a brain.

* * * * *